(12) United States Patent
Park

(10) Patent No.: US 11,879,010 B2
(45) Date of Patent: Jan. 23, 2024

(54) METHODS AND COMPOSITIONS FOR PRETARGETED IMMUNOTHERAPY

(71) Applicant: The Charlotte Mecklenburg Hospital Authority, Charlotte, NC (US)

(72) Inventor: Steven Park, Cary, NC (US)

(73) Assignee: The Charlotte Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 17/934,645

(22) Filed: Sep. 23, 2022

(65) Prior Publication Data

US 2023/0101939 A1 Mar. 30, 2023

Related U.S. Application Data

(60) Provisional application No. 63/250,597, filed on Sep. 30, 2021.

(51) Int. Cl.
| | | |
|---|---|---|
| *C07K 16/22* | (2006.01) | |
| *C07K 16/28* | (2006.01) | |
| *C12N 5/0783* | (2010.01) | |
| *A61K 39/00* | (2006.01) | |

(52) U.S. Cl.
CPC .......... *C07K 16/22* (2013.01); *C07K 16/2896* (2013.01); *C12N 5/0638* (2013.01); *A61K 2039/505* (2013.01); *A61K 2039/5158* (2013.01); *C12N 2510/00* (2013.01)

(58) Field of Classification Search
None
See application file for complete search history.

(56) References Cited

U.S. PATENT DOCUMENTS

| | | |
|---|---|---|
| 4,474,893 A | 10/1984 | Reading |
| 4,501,729 A | 2/1985 | Boucher et al. |
| 4,676,980 A | 6/1987 | Segal et al. |
| 4,816,567 A | 3/1989 | Cabilly et al. |
| 6,420,377 B1 | 7/2002 | Lee et al. |
| 6,537,988 B2 | 3/2003 | Lee |
| 7,442,507 B2 | 10/2008 | Polsky et al. |
| 7,572,631 B2 | 8/2009 | Berenson et al. |
| 8,076,496 B2 | 12/2011 | Saxon et al. |
| 8,519,122 B2 | 8/2013 | Jewett et al. |
| 8,703,936 B2 | 4/2014 | Jewett et al. |
| 2008/0279813 A1 | 11/2008 | Hall et al. |

FOREIGN PATENT DOCUMENTS

| | | |
|---|---|---|
| WO | 2004048557 A1 | 6/2004 |
| WO | 2008033403 A2 | 3/2008 |
| WO | 2008141275 A1 | 11/2008 |

(Continued)

OTHER PUBLICATIONS

Wang et al., ACS Chem. Biol. 2021, 16, 4, 724-730 (Year: 2021).*

(Continued)

*Primary Examiner* — Karl J Puttlitz
(74) *Attorney, Agent, or Firm* — Myers Bigel, P.A.

(57) ABSTRACT

This invention relates to methods and compositions comprising antibodies or fragments thereof comprising a targeting ligand and engineered cytotoxic cells comprising a targeting agent specific for the targeting ligand, for use in inducing cytotoxicity in a cancer cell, in delivering a cytotoxic cell to a cancer cell in a subject, and in treating cancer.

12 Claims, 11 Drawing Sheets

(56) References Cited

FOREIGN PATENT DOCUMENTS

| WO | 2009073513 A1 | 6/2009 |
|---|---|---|
| WO | 2009131712 A2 | 10/2009 |

OTHER PUBLICATIONS

Han et al., J Hematol Oncol 12, 128 (2019) (Year: 2019).*
Product: Click-&-Go Lys-to-Lys Protein-Protein Conjugation Kit, Click Chemistry Tools, 2019 (Year: 2019).*
Selvaraj et al., Curr Opin Chem Biol. Oct. 2013 ; 17(5): 753-760 (Year: 2013).*
Johann et al., Polym. Chem., 2020, 11, 4396-4407 (Year: 2020).*
Saini et al., Cancer Treatment Reviews 37 (2011) 385-390 (Year: 2011).*
Bird et al. "Single-Chain Antigen-Binding Proteins" Science, 242(4877):423-426 (1988).
Finn, Olivera J. "Human Tumor Antigens Yesterday, Today, and Tomorrow" Cancer Immunology Research, 5(5):347-354 (2107).
Holliger et al. "'Diabodies': Small bivalent and bispecific antibody fragments" Proceedings of the National Academy of Sciences USA, 90:6444-6448 (1993).
Huse et al. "Generation of a Large Combinatorial Library of the Immunoglobulin Repertoire in Phage Lambda" Science, 246(4935):1275-1281 (1989).
Huston et al. "Protein engineering of antibody binding sites: recovery of specific activity in an anti-digoxin single-chain Fv analogue produced in *Escherichia coli*" Proceedings of the National Academy of Sciences USA, 85:5879-5883 (1988).
Kang et al. "Antibody redesign by chain shuffling from random combinatorial Immunoglobulin libraries" Proceedings of the National Academy of Sciences USA, 88:11120-11123 (1991).
Kohler et al. "Continuous cultures of fused cells secreting antibody of predefined specificity" Nature, 256:495-497 (1975).
McKay et al. "Click Chemistry in Complex Mixtures: Bioorthogonal Bioconjugation" Chemistry & Biology, 21(9):1075-1101 (2014).
Morrison et al. "Chimeric human antibody molecules: Mouse antigen-binding domains with human constant region domains" Proceedings of the National Academy of Sciences USA, 81:6851-6855 (1984).
Neuberger et al. "Recombinant antibodies possessing novel effector functions" Nature, 312:604-608 (1984).
Novellino et al. "A listing of human tumor antigens recognized by T cells: Mar. 2004 update" Cancer Immunology, Immunotherapy, 54(3):187-207 (2005).
Prescher et al. "Chemical remodelling of cell surfaces in living animals" Nature, 430(7002):873-877 (2004).
Rosenberg, Steven A. "The Immunotherapy of Solid Cancers Based on Cloning the Genes Encoding Tumor-Rejection Antigens" Annual Review of Medicine, 47:481-491 (1996).
Sletten et al. "Bioorthogonal chemistry: fishing for selectivity in a sea of functionality" Angewandte Chemie International Edition, 48(38):6974-6998 (2009).
Takeda et al. "Construction of chimaeric processed immunoglobulin genes containing mouse variable and human constant region sequences" Nature, 314:452-454 (1985).
Tyle, Praveen "Iontophoretic Devices for Drug Delivery" Pharmaceutical Research, 3:318-326 (1986).
Vigneron et al. "Database of T cell-defined human tumor antigens: the 2013 update" Cancer Immunity, 13(15):1-6 (2013).
Walker et al. "Interaction of human IgG chimeric antibodies with the human FcRI and FcRII receptors: requirements for antibody-mediated host cell-target cell interaction" Molecular Immunology, 26:403-411 (1989).
Ward et al. "Binding activities of a repertoire of single immunoglobulin variable domains secreted from *Escherichia coli*" Nature, 341(6242):544-546 (1989).

* cited by examiner

METHODS AND COMPOSITIONS FOR PRETARGETED IMMUNOTHERAPY

PRIORITY STATEMENT

This application claims the benefit, under 35 U.S.C. § 119(e), of U.S. Provisional Application Ser. No. 63/250,597, filed Sep. 30, 2021, the entire contents of which are incorporated by reference herein.

FIELD OF THE INVENTION

This invention relates to methods and compositions comprising antibodies or fragments thereof comprising a targeting ligand and engineered cytotoxic cells comprising a targeting agent specific for the targeting ligand, for use in inducing cytotoxicity in a cancer cell, in delivering a cytotoxic cell to a cancer cell in a subject, and in treating cancer.

BACKGROUND OF THE INVENTION

Chimeric Antigen Receptor (CAR) T-cell and -natural killer (NK) cell therapy have emerged as promising options for next generation cellular immunotherapy. A variation of CAR-T cell therapy, CAR-NK cell therapy is considered the most advanced form of targeted NK-cell therapy, but is limited by requiring genetic modification of NK cells, being of use to only one cancer type, and being susceptible to treatment resistance by the tumor via antigen shedding and/or antigen heterogeneity.

The present invention overcomes previous shortcomings in the art by providing methods and compositions for "off-the-shelf" pretargeted NK-cell mediated cancer therapy.

SUMMARY OF THE INVENTION

One aspect of the invention relates to a method of inducing cytotoxicity in a cancer cell, the method comprising: (a) contacting the cancer cell with a first antibody or fragment thereof, wherein the first antibody or fragment thereof comprises a first antigen binding portion and a targeting ligand and wherein the cancer cell comprises a first antigen on the surface of the cancer cell, under conditions whereby the first antigen binding portion of the first antibody or fragment thereof binds the first antigen on the surface of the cancer cell; and (b) contacting the cancer cell of step (a) with a cytotoxic cell comprising a targeting agent specific for the targeting ligand, under conditions whereby the targeting agent binds the targeting ligand, thereby inducing cytotoxicity in the cancer cell.

Another aspect of the invention relates to a method of delivering a cytotoxic cell to a cancer cell, the method comprising: (a) contacting the cancer cell with a first antibody or fragment thereof, wherein the first antibody or fragment thereof comprises a first antigen binding portion and a targeting ligand and wherein the cancer cell comprises a first antigen on the surface of the cancer cell, wherein the first antigen binding portion of the first antibody or fragment thereof binds the first antigen on the surface of the cancer cell; and (b) contacting the cancer cell of step (a) with a cytotoxic cell comprising a targeting agent specific for the targeting ligand, wherein the targeting agent binds the targeting ligand, thereby delivering the cytotoxic cell to the cancer.

Another aspect of the invention relates to a method of treating cancer in a subject in need thereof, comprising: (a) administering to the subject an effective amount of a first antibody or fragment thereof, wherein the first antibody or fragment thereof comprises a first antigen binding portion specific for a first cancer antigen and a targeting ligand, and wherein the cancer comprises the first cancer antigen specific for the first antigen binding portion, wherein the first antigen binding portion of the first antibody or fragment thereof binds the first cancer antigen; and (b) administering to the subject of (a) an effective amount of a cytotoxic cell comprising a targeting agent specific for the targeting ligand, wherein the targeting agent binds the targeting ligand, thereby treating the cancer in the subject.

Another aspect of the invention relates to a method of making a cytotoxic cell of the invention, comprising: incubating an unmodified cytotoxic cell with a first reaction agent comprising a functional group to produce a cytotoxic cell expressing the functional group on the surface of the cell, thereby modifying the cytotoxic cell to express the functional group on the surface of the cytotoxic cell.

Another aspect of the invention relates to a method of making a cytotoxic cell of the invention, comprising incubating an unmodified cytotoxic cell with a first reaction agent comprising a functional group to produce a cytotoxic cell expressing the functional group on the surface of the cell, and further optionally incubating the functional group-expressing cytotoxic cell with a second reaction agent which produces a targeting agent upon reaction, under conditions whereby the functional group on the surface of the cytotoxic cell is replaced with the targeting agent of the second reaction to produce a cytotoxic cell expressing the targeting agent, thereby modifying the cytotoxic cell to express the targeting agent on the surface of the cytotoxic cell.

Also provided are compositions, pharmaceutical compositions, and kits comprising the antibody or fragment thereof and/or cytotoxic cell of the present invention.

Additionally provided are methods of use of the cytotoxic cell and/or antibody or fragment thereof of the invention, e.g., in inducing cytotoxicity in a cancer cell, in delivering a cytotoxic cell to a cancer cell in a subject, and/or in treating cancer.

Additionally provided are methods of preparation of a medicament for use comprising a cytotoxic cell and/or antibody or fragment thereof of the invention.

DETAILED DESCRIPTION

Figure 1:
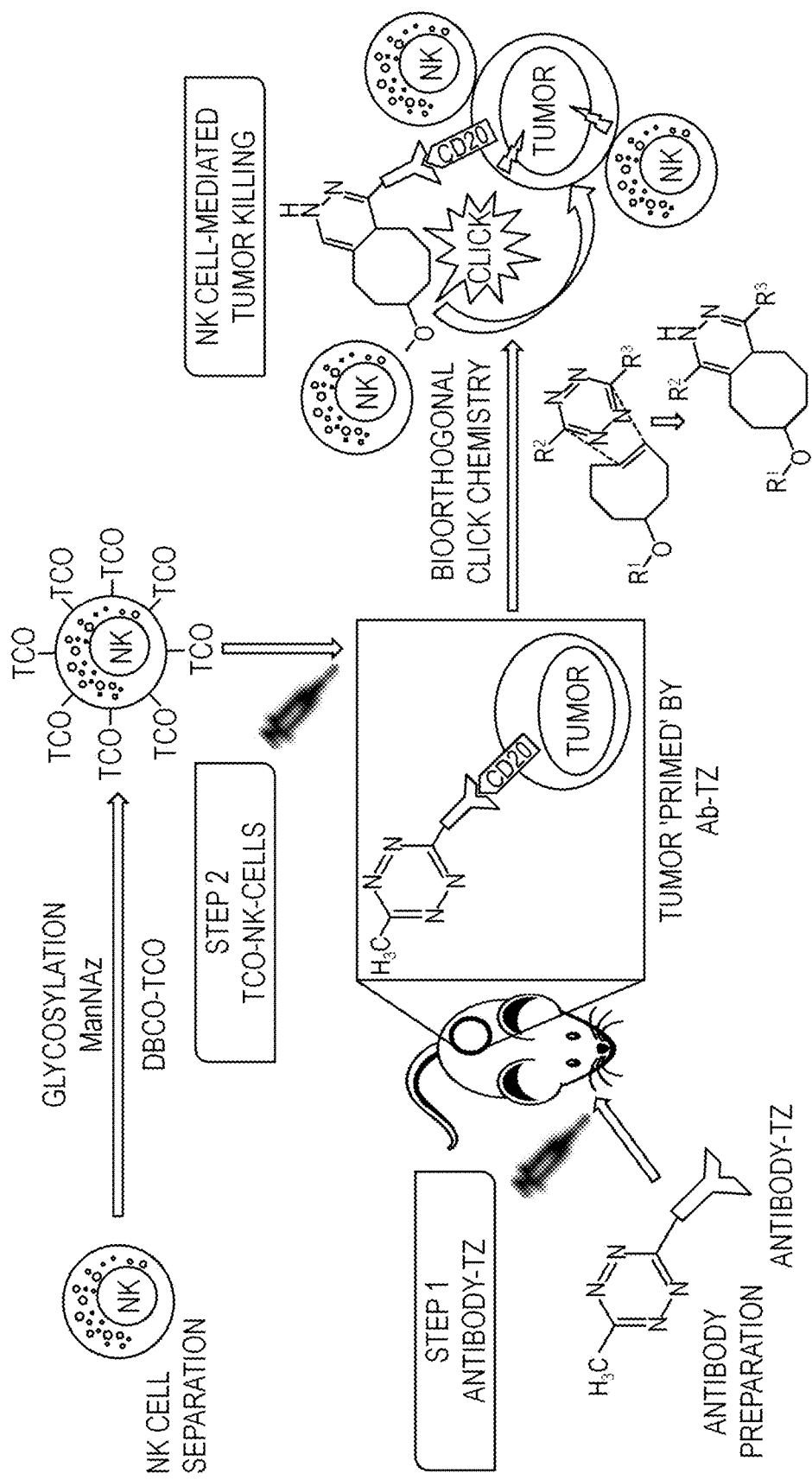
FIG. 1 shows a cartoon of the method protocol. A target tumor cell is primed with antibody-tetrazine (TZ). NK-cells functionalized with TCO are then injected, and upon the contact with the target tumor cells, TCO on the surface of NK cell undergoes a rapid IEDDA reaction with TZ on the surface of tumor cell via click chemistry. The high-affinity chemical bond between TCO-TZ anchors NK cell on the target tumor cells and allows enhanced antibody-dependent cellular cytotoxicity (ADCC), leading to effective tumor cell killing.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations, and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, "one or more" means one, two, three, four, five, six, seven, eight, nine, ten, 11, 12, 13, 14, 15, 16, 17, 18, 19, 20, etc.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The term "contact" or grammatical variations thereof as used with respect to an antibody or fragment thereof and/or a cytotoxic cell, refers to bringing the antibody or fragment thereof and/or the cytotoxic cell in sufficiently close proximity to each other for one to exert a biological effect on the other. Alternatively, it may also be used herein to refer to bringing the antibody or fragment thereof and/or the cytotoxic cell in sufficiently close proximity to a cell (e.g., of a subject, e.g., a cancer cell) for either and/or both the antibody or fragment thereof and/or the cytotoxic cell of the invention to exert a biological effect on the cell.

The term "administering" or "administration" of a composition of the present invention to a subject includes any route of introducing or delivering to a subject a compound to perform its intended function.

A "sample", "biological sample", and/or "ex vivo sample" of this invention can be any biological material, such as a biological fluid, an extract from a cell, an extracellular matrix isolated from a cell, a cell (in solution or bound to a solid support), a tissue, a tissue homogenate, and the like as are well known in the art.

By the terms "treat," "treating," or "treatment of," it is intended that the severity of the subject's condition is reduced or at least partially improved or modified and that some alleviation, mitigation or decrease in at least one clinical symptom is achieved.

As used herein, the terms "prophylactic" or "preventative" treatment can include preventing at least one symptom of the disorder, disease or condition, i.e., causing a clinical symptom to not significantly develop in a subject that may develop or be predisposed to the disease but does not yet experience or display symptoms of the disease or condition.

"Subject" as used herein includes any animal in which treatment with a method and/or composition disclosed herein is necessary or desired. In some embodiments, the subject is any animal that can receive a beneficial and/or therapeutic effect from administration of an antibody or fragment thereof and/or a cytotoxic cell of the present invention. Suitable subjects include, but are not limited to, mammals. The term "mammal" as used herein includes, but is not limited to, humans, primates, non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a composition including those described herein. For example, in particular embodiments, the subject has (or has had) or is at risk for a cancer. As a further option, the subject can be a laboratory animal and/or an animal model of disease. In some embodiments, the subject is a mammal and in particular embodiments, the subject is a human of any age, race, gender, or ethnicity, etc. In some embodiments, the subject may be a human patient.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

A "subject in need" of the methods of the invention can be a subject known to have, suspected of having, or at risk of having cancer.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "therapeutically effective" or "effective" amount as used herein is an amount that provides some improvement or benefit to the subject. Alternatively stated, a "therapeutically effective" amount or an "effective amount" is an amount that will provide some alleviation, mitigation, or decrease in at least one clinical symptom in the subject. Those skilled in the art will appreciate that the effects need not be complete or curative, as long as some benefit is provided to the subject.

A "prophylactically effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

As used herein, "modulate," "modulates" or "modulation" refers to enhancement (e.g., an increase) or inhibition (e.g., diminished, reduced or suppressed) of the specified activity.

The term "enhancement," "enhance," "enhances," or "enhancing" refers to an increase in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or an increase in the specified activity of at least about 5%, 10%, 25%, 35%, 40%, 50%, 60%, 75%, 80%, 90%, 95%, 97%, 98%, 99% or 100%.

The term "inhibit," "diminish," "reduce" or "suppress" or grammatical variations thereof as used herein refers to a decrease in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or a decrease or reduction in the specified activity of at least about 5%, 10%, 25%, 35%, 40%, 50%, 60%, 75%, 80%, 90%, 95%, 97%, 98%, 99% or 100%. These terms are intended to be relative to a reference or control. In particular embodiments, the inhibition or reduction results in little or essentially no detectable activity (at most, an insignificant amount, e.g., less than about 10% or even 5%).

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., Glossary of Genetics: Classical and Molecular, 5th Ed., Springer-Verlag: New York, 1991, and Lewin, Genes V, Oxford University Press: New York, 1994. The definitions provided herein are to facilitate understanding of certain terms used frequently herein and are not meant to limit the scope of the application.

"Pharmaceutically acceptable" as used herein means that the compound or composition is suitable for administration to a subject to achieve the treatments described herein, without unduly deleterious side effects in light of the severity of the disease and necessity of the treatment.

Pharmaceutical formulations comprising the antibodies or fragments thereof, cytotoxic cells and/or compositions of the invention and a pharmaceutically acceptable carrier are also provided, and can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of the invention is typically admixed with, inter alia, a pharmaceutically acceptable carrier. The carrier may be a solid or a liquid, or both, and is preferably formulated with the composition of the invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

"Antibody" or "antibodies" as used herein refers to all types of immunoglobulins, including IgG, IgM, IgA, IgD, and IgE. The term "immunoglobulin" includes the subtypes of these immunoglobulins, such as $IgG_1$, $IgG_2$, $IgG_3$, $IgG_4$, etc. The antibodies may be of any species of origin, including (for example) mouse, rat, rabbit, horse, or human, or may be chimeric or humanized antibodies. The term "antibody" as used herein includes antibody fragments which retain the capability of binding to a target antigen, for example, Fab, $F(ab')_2$, and Fv fragments, and the corresponding fragments obtained from antibodies other than IgG. Such fragments are also produced by known techniques. In some embodiments antibodies may be coupled to or conjugated to a detectable group or therapeutic group in accordance with known techniques.

Furthermore, the term "antibody" as used herein, is intended to refer to immunoglobulin molecules comprising four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementary determining regions (CDR), interspersed with regions that are more conserved, termed framework regions (FR). In various embodiments of the antibody or antigen binding fragment thereof of the invention, the FRs may be identical to the human germline sequences, or may be naturally or artificially modified. Each VH and VL is composed of three CDRs and four FRs, arranged from amino-terminus to carboxy-terminus in the following order: FR1, CDR1, FR2, CDR2, FR3, CDR3, FR4.

Thus, as used herein, the term "antibody" includes intact immunoglobulin molecules as well as active fragments thereof, such as Fab, $F(ab')_2$, and Fc, which are capable of binding the epitopic determinant of an antigen (i.e., antigenic determinant The terms "antibody" and "antibodies" as used herein refer to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, and/or can be a chimeric or humanized antibody. See, e.g., Walker et al., *Molec. Immunol.* 26:403-11 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980. The antibody can further be a single chain antibody (scFv) or bispecific antibody.

Techniques for the production of chimeric antibodies or humanized antibodies by splicing mouse antibody genes to human antibody genes to obtain a molecule with appropriate antigen specificity and biological activity can be used (Morrison et al. 1984. Proc. Natl. Acad. Sci. 81:6851-6855; Neuberger et al. 1984. Nature 312:604-608; Takeda et al. 1985. Nature 314:452-454). Alternatively, techniques described for the production of single chain antibodies can be adapted, using methods known in the art, to produce single chain antibodies specific for antigens of this invention. Antibodies with related specificity, but of distinct idiotypic composition, can be generated by chain shuffling from random combinatorial immunoglobulin libraries (Burton 1991. *Proc. Natl. Acad. Sci.* 88:11120-3).

In general, the antibodies and antigen binding fragments thereof of the present invention possess very high affinities, typically possessing $K_D$ values of from about $10^{-8}$ through about $10^{-12}$ M or higher, for example, at least $10^{-8}$ M, at least $10^{-9}$ M, at least $10^{-10}$ M, at least $10^{-11}$ M, or at least $10^{-12}$ M, when measured by binding to antigen presented on cell surface.

The antibodies and antigen binding fragments thereof of the present invention possess very high affinities, typically possessing $EC_{50}$ values of from about $10^{-8}$ through about $10^{-12}$ M or higher, for example, at least $10^{-8}$ M, at least $10^{-9}$ M, at least $10^{10}$ M, at least $10^{-1}$ M, or at least $10^{-12}$ M, when measured by binding to antigen presented on cell surface.

As used herein, the term "binding portion" refers to the portion (e.g., fragment) of a molecule which binds to another molecule (e.g., a target). For example, an "antigen binding portion" as used herein refers to a portion of a molecule which is capable of binding to the antigen. The binding portion may be, e.g., isolated from a molecule or compound, synthetically generated de novo, and/or comprised within a larger molecule (e.g., an antibody or fragment thereof).

As used herein, the term "antigen" refers to a molecule capable of inducing the production of immunoglobulins (e.g., antibodies). A molecule capable of antibody and/or immune response stimulation may be referred to as antigenic and/or immunogenic, and can be said to have the ability of antigenicity/immunogenicity. The binding site for an antigen comprised in an antibody may be referred to as an antigen binding portion. An antigen binding portion may be, e.g., isolated from an antibody, synthetically generated de novo, and/or comprised within a larger molecule (e.g., an antibody or fragment thereof).

The term "antigen-binding portion" or "antigen-binding fragment" of an antibody (or simply "antibody portion" or "antibody fragment"), as used herein, refers to one or more fragments, portions or domains of an antibody that retain the ability to specifically bind to an antigen. It has been shown that fragments of a full-length antibody can perform the antigen-binding function of an antibody. Examples of binding fragments encompassed within the term "antigen-binding portion" of an antibody include (i) an Fab fragment, a monovalent fragment consisting of the VL, VH, CL1 and CH1 domains; (ii) an F(ab')$_2$ fragment, a bivalent fragment comprising two F(ab)' fragments linked by a disulfide bridge at the hinge region; (iii) an Fd fragment consisting of the VH and CH1 domains; (iv) an Fv fragment consisting of the VL and VH domains of a single arm of an antibody; (v) a dAb fragment (Ward et al. (1989) Nature 241:544-546), which consists of a VH domain; and (vi) an isolated complementary determining region (CDR). Furthermore, although the two domains of the Fv fragment, VL and VH, are coded for by separate genes, they can be joined, using recombinant methods, by a synthetic linker that enables them to be made as a single contiguous chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies, are also encompassed (see e.g., Holliger et al. (1993) *Proc. Natl. Acad Sci. USA* 90:6444-6448).

The term "epitope" refers to an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of one (or more) linear polypeptide chain(s). A linear epitope is an epitope produced by adjacent amino acid residues in a polypeptide chain. In certain embodiments, an epitope may include other moieties, such as saccharides, phosphoryl groups, or sulfonyl groups on the antigen.

As used herein, terms "click chemistry," "bio-orthogonal chemistry" or "bio-orthogonal reaction" refer to any chemical reaction that can be carried out in a live system (e.g., in vivo without interfering with any other natural biological and/or chemical processes Reactions referred to as "click chemistry" and/or "bio-orthogonal" are generally highly efficient and stereospecific, allowing for easy product isolation and include Staudinger ligation, 1,3-diolar cycloaddition, copper-catalyzed azide-alkyne cycloaddition (CuAAC), quadricyclane ligation, inverse-demand Diels-Alder cycloaddition (IEDDA), and strain-promoted azide-alkyne cycloaddition (SPAAC), among others. Click chemistry, bio-orthogonal chemistry, the history thereof and application thereof are further described in Prescher et al. 2004 Nature 430(7002):873-877; Sletten and Bertozzi, 2009 *Angew Chem Int Ed Engl* 48(38):6974-6998; McKay and Finn, 2014 *Chemistry & Biology* 21(9):1075-1101; and U.S. Pat. Nos. 8,076,496; 8,519,122; and 8,703,936; the disclosures of each of which are incorporated herein by reference. Methods of Using Antibodies or Fragments Thereof and/or Cytotoxic Cells of the Invention and Compositions Comprising the Same.

The present invention relates, in part, to compositions and methods of comprising antibodies or fragments thereof comprising a targeting ligand and engineered cytotoxic cells comprising a targeting agent specific for the targeting ligand, for use in inducing cytotoxicity in a cancer cell, in delivering a cytotoxic cell to a cancer cell in a subject, and in treating cancer.

Recent advances in cellular immunotherapy include Chimeric Antigen Receptor (CAR) T-cell therapy. Natural killer (NK) cell therapy has emerged as a promising option for next generation cellular immunotherapy due to a number of advantages. While not wishing to be bound to theory, NK cells are associated with less risk of graft versus host effects, are less likely to cause cytokine release syndrome (CRS) than T cell based therapy, and can be generated from different sources. In addition, NK cells are more active than T cells against solid tumors than T cell based therapies and do not require HLA matching.

However, current NK-cell therapy typically utilizes NK cells that are not specific to the target tumor, limiting safety as well as efficacy in cancer treatment. A variation of CAR-T cell therapy, CAR-NK cell therapy is considered the most advanced form of targeted NK-cell therapy, but is limited by requiring genetic modification of NK cells, being of use to only one cancer type (e.g., CD19 CAR-NK cells can only be used for CD19+ lymphoma), and being susceptible to treatment resistance by the tumor via antigen shedding and/or antigen heterogeneity.

The present invention applies bioorthogonal 'click' chemistry by functionalizing antibodies and cytotoxic immune effector cells (e.g., NK cells) with a ligation pair to kill cancer cells in a highly targeted manner. 'click" chemistry is a class of biocompatible small molecule reactions commonly used in bioconjugation. Thus, the present invention uses simple and quick glycoengineering to modify the NK cell surface instead of genetic modifications. Without wishing to be bound to theory, the glycoengineered cytotoxic cells of the invention are able to recognize any target tumors 'primed' by the antibodies of the present invention functionalized with a corresponding orthogonal ligation pair. Accordingly, the invention allows 'off-the-shelf' cellular immunotherapy by obviating the need to generate different NK cell therapies for different tumor types.

Thus, one aspect of the invention provides a method of inducing cytotoxicity in a cancer cell, the method comprising: (a) contacting the cancer cell with a first antibody or fragment thereof, wherein the first antibody or fragment thereof comprises a first antigen binding portion and a targeting ligand and wherein the cancer cell comprises a first antigen on the surface of the cancer cell, under conditions whereby the first antigen binding portion of the first antibody or fragment thereof binds the first antigen on the surface of the cancer cell; and (b) contacting the cancer cell of step (a) with a cytotoxic cell comprising a targeting agent specific for the targeting ligand, under conditions whereby the targeting agent binds the targeting ligand (e.g., via an inverse-demand Diels-Alder cycloaddition (IEDDA) reaction, e.g., via a strain-promoted azide-alkyne cycloaddition (SPAAC) reaction), thereby inducing cytotoxicity in the cancer cell.

Another aspect of the invention provides a method of delivering a cytotoxic cell to a cancer cell, the method comprising: (a) contacting the cancer cell with a first antibody or fragment thereof, wherein the first antibody or fragment thereof comprises a first antigen binding portion and a targeting ligand and wherein the cancer cell comprises a first antigen on the surface of the cancer cell, wherein the first antigen binding portion of the first antibody or fragment thereof binds the first antigen on the surface of the cancer cell; and (b) contacting the cancer cell of step (a) with a cytotoxic cell comprising a targeting agent specific for the targeting ligand, wherein the targeting agent binds the targeting ligand (e.g., via an inverse-demand Diels-Alder cycloaddition (IEDDA) reaction, e.g., via a strain-promoted azide-alkyne cycloaddition (SPAAC) reaction), thereby delivering the cytotoxic cell to the cancer.

In some embodiments, the cancer cell may be in a subject such as a subject having, suspected of having, and/or at risk of cancer.

Thus, another aspect of the invention provides a method of treating cancer in a subject in need thereof, comprising: (a) administering to the subject an effective amount of a first antibody or fragment thereof, wherein the first antibody or fragment thereof comprises a first antigen binding portion specific for a first cancer antigen and a targeting ligand, and wherein the cancer comprises the first cancer antigen specific for the first antigen binding portion (e.g., on the surface one or more cancer cells), wherein the first antigen binding portion of the first antibody or fragment thereof binds the first cancer antigen (e.g., on the surface of the one or more cancer cells); and (b) administering to the subject of (a) an effective amount of a cytotoxic cell comprising a targeting agent specific for the targeting ligand, wherein the targeting agent binds the targeting ligand (e.g., via an inverse-demand Diels-Alder cycloaddition (IEDDA) reaction, e.g., via a strain-promoted azide-alkyne cycloaddition (SPAAC) reaction), thereby treating the cancer in the subject.

Conditions whereby the targeting agent may bind the targeting ligand include conditions allowing for a biorthogonal reaction between the targeting ligand and the targeting agent specific for the targeting ligand, such as but not limited to via an inverse-demand Diels-Alder cycloaddition (IEDDA) reaction and/or a strain-promoted azide-alkyne cycloaddition (SPAAC) reaction). These and other reactions allowing for in vivo bio-orthogonal reactions are known in the art and may be alternatively referred to as "click chemistry."

In some embodiments, the methods of the invention may further comprise contacting with or administering a second or more (e.g., a third, a fourth, or more) antibody or fragment thereof different from said first antibody or fragment thereof, wherein each of the second or more antibody or fragment thereof comprises the same targeting ligand as the first antibody or fragment thereof, and a second or more antigen binding portion that is different from the first antigen binding portion of the first antibody or fragment thereof.

In some embodiments, the methods of the present invention may further comprise contacting with or administering a third antibody or fragment thereof different from the first antibody or fragment thereof and/or the second antibody or fragment thereof, wherein the third antibody or fragment thereof comprises the same targeting ligand as the first and/or the second antibody or fragment thereof and a third antigen binding portion that is different from the first and/or the second antigen binding portion of the first and the second antibody or fragment thereof. In some embodiments, the methods of the present invention may further comprise contacting with or administering a third antibody or fragment thereof different from the first antibody or fragment thereof and the second antibody or fragment thereof, wherein the third antibody or fragment thereof comprises the same targeting ligand as the first and the second antibody or fragment thereof and a third antigen binding portion that is different from the first and the second antigen binding portion of the first and the second antibody or fragment thereof.

The cytotoxic cell of the present invention may be any mammalian effector cell capable of inducing cell death in a target cell, such as but not limited to a mammalian innate and/or adaptive immune effector cell. In some embodiments, the cytotoxic cell may be a natural killer (NK) cell, a T cell (e.g., T helper cell, T cytotoxic cell (CTL), T gamma delta (γδ) cell, etc.), macrophage, or dendritic cell. In some embodiments, the cytotoxic cell may be an NK cell. In some embodiments, the cytotoxic cell may be a CTL. In some embodiments, the cytotoxic cell may be a macrophage. In some embodiments, the cytotoxic cell may be a dendritic cell.

The cytotoxic cell of the present invention may be obtained from a variety of methods including those known in the art such as, but not limited to, ex vivo isolation from a subject (e.g., a donor, e.g., an allogeneic donor), pre-established in vitro cell lines (e.g., NK92 cell line, e.g., Jurkat cell line), de novo generated immortalized cell lines (e.g., a mammalian primary cell (e.g., a primary NK cell) newly immortalized to establish a source of said cytotoxic cell), isolated stem cells, and/or induced pluripotent stem cells. In some embodiments, the cytotoxic cell may comprise a cytotoxic cell line (e.g., NK92 cell line or derivative thereof, e.g., Jurkat cell line or derivative thereof) modified to express the targeting agent. In some embodiments, the cytotoxic cell may comprise a cytotoxic cell from a donor (e.g., a donor that is related to the subject, e.g., a donor that is unrelated to the subject), modified ex vivo to express the targeting agent. In some embodiments, the cytotoxic cell may comprise a cytotoxic cell from the subject (e.g., an autologous cell), modified ex vivo to express the targeting agent.

In some embodiments, cytotoxic cells and/or other cells of use in the invention can be isolated from a blood sample and/or spleen of a subject, such as a donor or recipient subject, using standard methods including, e.g., Ficoll density gradient centrifugation followed by negative selection to remove undesired cells. Methods of isolating cells are known to those of skill in the art and include FACS sorting of cells. Immune cells can also be obtained from a subject using an apheresis procedure.

Non-limiting examples of an antibody or fragment thereof of the present invention include a monoclonal antibody or fragment thereof, a chimeric antibody or fragment thereof, a CDR-grafted antibody or fragment thereof, a humanized antibody or fragment thereof, an Fc, a Fab, a Fab', a F(ab')$_2$, a Fv, a disulfide linked Fv, a single chain antibody (scFv), a single domain antibody (dAb), a diabody, a multispecific antibody (e.g., a bispecific antibody) or fragment thereof, an anti-idiotypic antibody or fragment thereof, a bifunctional hybrid antibody or fragment thereof, a functionally active epitope-binding antibody fragment, an affibody, a nanobody, and any combination thereof.

Active antibody fragments included within the scope of the present invention include, for example, Fab, F(ab')$_2$, and Fe fragments, and the corresponding fragments obtained from antibodies other than IgG. Such fragments can be produced by known techniques. For example, F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse et al., (1989) *Science* 254:1275-1281).

Monoclonal antibodies can be produced in a hybridoma cell line according to the technique of Kohler and Milstein (Nature 265:495-97 (1975)). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) *Science* 246:1275-81.

In some embodiments, an antibody or fragment thereof (e.g., the first, second, third, or more antibody or fragment thereof) may comprise a monoclonal antibody, a Fab fragment, a Fab'-SH fragment, a FV fragment, a scFV fragment, a (Fab')$_2$ fragment, an Fc-fusion protein, an affibody, or any combination thereof.

Non-limiting examples of targeting ligands include streptavidin (SA), dibenzylcyclooctyne (DBCO), tetrazine, bicyclononyne (BCN), trans-cyclooctene (TCO), and any combination thereof. The targeting agent may be any agent which is specific for a targeting ligand of the invention, including but not limited to biotin, azide (Az), cyclopropene (Cp), trans-cyclooctene (TCO), tetrazine, and any combination thereof.

In some embodiments, the targeting agent and the targeting ligand of the invention may comprise a bio-orthogonal ligation pair (e.g., tetrazine and TCO).

Nonlimiting examples of a cancer antigen that can be targeted according to methods of this invention include NY-ESO-1, WT-1, MART-1, gp100, gp75, MAGEA3, MAGEA4, HPV16-E6, thyroglobulin, melanoma-associated antigen tyrosinase, CD45, CD16, HLA-DR, alpha-4 integrin, CD19, CD22, CD23, CD5, CD30, CD70, CD38, CD138, CD20, CD123, HER2, IL13Rα2, CSPG4, EGFR, EGFRvIII, mesothelin, PSMA (prostate-specific membrane antigen, encoded by the FOLH1 (folate hydrolase 1) gene), CEA (carcinoembryonic antigen), GD2 (disialoganglioside 2), GPC3 (glypican-3), CAIX (carbonic anhydrase IX), L1-CAM (L1 cell adhesion molecule), CA125 (cancer antigen 125, also known as MUC16), CD133 (prominin-1), FAP (fibroblast activation protein), MUC1 (mucin 1), FR-α (folate receptor-α), Lewis-Y, folate receptor p, DKK1, integrin P, other members of the MAGEA family (melanoma antigen family A), including for example, MAGEA1 which comprises members of the larger family of cancer testis (CT) or cancer-germline antigen family, tumor peptides derived from cyclin B1, human cancer antigens targeted by CD4+ T cells, GAGE and BAGE antigens, hTERT, PSA, survivin, p53, mutated antigens derived from the protein products of mutated oncogenes such as KRAS, NRAS, and HRAS, new epitopes created by gene translocations and fusions such as BCR-ABL in chronic myelogenous leukemia, ETV6/AML in acute lymphoblastic leukemia, NPM/ALK in anaplastic large-cell lymphomas and ALK in neuroblastomas, cancer neoantigens, including neoantigens that arise in cancer with high mutator phenotype, and any combination thereof. A cancer antigen of this invention can be any cancer antigen now known or later identified, including for examples, antigens listed in the following references: Novellino et al. "A listing of human tumor antigens recognized by T cells: March 2004 update" *Cancer Immunology, Immunotherapy* 54(3):187-207 (2005); Vigneron et al. "Database of T cell-defined human tumor antigens: the 2013 update" *Cancer Immunity* 13:15 (2013); Finn. "Human Tumor Antigens Yesterday, Today, and Tomorrow." *Cancer Immunol Res* 5(5):347-354 (2107); and the database maintained at cancerresearch.org/scientists/meetings-and-resources/peptide-database, the entire contents of each of which are incorporated by reference herein. In some embodiments, the cancer antigen (e.g., the first, second, or more cancer antigen) may be HER2, EGFR, CD19, CD20, CD45, CD16, HLA-DR, alpha-4 integrin, or any combination thereof.

An antigen binding portion of the present invention (e.g., the first, second, third, or more antigen binding portion) may target and/or bind to any relevant antigen of use in the present invention. In some embodiments, an antigen binding portion of the present invention may be specific for a cancer antigen, e.g., an anticancer antigen binding portion. In some embodiments, the antigen binding portion (e.g., the first, second, or more antigen binding portion) is an anti-HER2, EGFR, CD19, CD16, HLA-DR or alpha-4 integrin binding portion, or any combination thereof.

The implementation of the methods of the present invention may be for either "prophylactic" or "therapeutic" purpose. When provided prophylactically, therapy can be provided in advance of any symptom. The prophylactic administration of the therapy serves to prevent development of cancer. Prophylactic administration may be given to a subject "in need thereof," which can be a subject that is at risk of cancer due to, for example, a family history of cancer, or a previous cancer episode. Alternatively, the antibody or fragment thereof comprising a targeting ligand and cytotoxic cells comprising a targeting agent specific to the targeting ligand may be given to a subject with changing (e.g., rising) cancer marker levels. Multiple biomarkers for particular cancers are known in the art. For example, melanoma markers are described in PCT Publications WO 2008/141275, WO 2009/073513, or in U.S. Pat. No. 7,442,507.

Methods for administering cells are well known to those of skill in the art, including, e.g., as described in WO 2004/048557; WO 2008/033403; U.S. 2008/0279813 WO2008/033403; U.S. Pat. No. 7,572,631; and WO 2009/131712, which are all herein incorporated by reference in their entirety. The amount of cells that will be effective in the treatment and/or suppression of cancer may be determined by standard clinical techniques. The dosage will depend on the type of cancer to be treated, the severity and course of the cancer, previous therapy the recipient has undergone and/or is undergoing, the recipient's clinical history, and the discretion of the attending physician. The antibody or fragment thereof and/or the cytotoxic cell may be administered in various treatment regimens, e.g., a single or a few doses over one to several days to ameliorate symptoms and/or periodic doses over an extended time to inhibit cancer progression, to reduce cancer presence, and/or to prevent cancer recurrence. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

The methods described herein are useful for the treatment of any type of cancer in a subject. As used herein, the term "cancer" includes any type of cancer. A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a subject, or may be a non-tumorigenic cancer cell, such as a leukemia cell. Non-limiting examples of a cancer of this invention include B cell lymphoma, T cell lymphoma, myeloma, leukemia, hematopoietic neoplasias, thymoma, lymphoma, sarcoma, lung cancer, liver cancer, non-Hodgkins lymphoma, Hodgkins lymphoma, uterine cancer, cervical cancer, endometrial cancer, adenocarcinoma, breast cancer, pancreatic cancer, colon cancer, anal cancer, renal cancer, bladder cancer, prostate cancer, ovarian cancer, primary or metastatic melanoma, squamous cell carcinoma, basal cell carcinoma, brain cancer, angiosarcoma, hemangiosarcoma, head and neck carcinoma, thyroid carcinoma, soft tissue sarcoma, bone sarcoma, testicular cancer, gastrointestinal cancer, stomach cancer, glioblastoma, small cell lung cancer, non-small cell lung cancer and any combination thereof, as well as any other cancer or malignant neoplasm now known or later identified (see, e.g., Rosenberg (1996) Ann. Rev. Med. 47:481-491, the entire contents of which are incorporated by reference herein). In some embodiments, a cancer of the present invention may be breast cancer (e.g., BRCA+, HER2+, triple negative, etc.), lung cancer, lymphoma, colon cancer, prostate cancer, leukemia, multiple myeloma, or any combination thereof.

In some embodiments, an antibody or fragment thereof of the invention (e.g., a first, second, and/or third or more antibody or fragment thereof) may be administered to a subject prior to, concurrently with, and/or after a cytotoxic cell of the present invention is administered to a subject. For example, in some embodiments, an antibody or fragment thereof of the invention may be administered to a subject about 1, 2, or 3 days or about 72, 50, 48, 24, 20, 18, 12, 6, 4, 2, or 1 hour(s) before administration of a cytotoxic cell of the present invention to the subject.

The first, second, third, or more antibody or fragment thereof and/or cytotoxic cell of the present invention may be formulated for administration in a pharmaceutical carrier in accordance with known techniques. See, e.g., Remington, *The Science And Practice of Pharmacy* (latest edition). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the subject. The carrier may be a liquid and is preferably formulated with the compound as a unit-dose formulation which may contain from 0.01 or 0.5% to 95% or 99% by weight of the active compound. The carrier may be sterile or otherwise free from contaminants that would be undesirable to administer or deliver to a subject.

In addition, cells of the invention and/or populations of the cells of this invention can be cryopreserved and thawed prior to administration to a subject.

Formulations of the present invention suitable for parenteral administration comprise sterile aqueous and non-aqueous injection solutions of the active compound, which preparations are preferably isotonic with the blood of the intended subject. These preparations may contain anti-oxidants, buffers, bacteriostats and solutes which render the formulation isotonic with the blood of the intended subject.

The active agents of the invention may be administered by any medically appropriate procedure, including but not limited to, intravenous, intratumor, intraperitoneal and/or intra-arterial administration. In some embodiments, the administering step may be via a route selected from the group consisting of intravenous, intramuscular, subcutaneous, topical, oral, transdermal, intraperitoneal, intrathecal, intraventricular, intravitreal, intraocular, intraorbital, intranasal, by implantation, by inhalation, by intratumoral, and any combination thereof.

Active agents of the invention may be provided in lyophylized form in a sterile aseptic container or may be provided in a pharmaceutical formulation in combination with a pharmaceutically acceptable carrier, such as sterile pyrogen-free water or sterile pyrogen-free physiological saline solution.

Dosage of the agents and compositions of this invention for the methods of use described herein will depend, among other things, on the condition of the subject, the particular disorder being treated, the route of administration, the nature of the therapeutic agent employed, and the sensitivity of the subject to the particular agent(s).

In some embodiments, the cytotoxic cells can be in a volume of a liter or less, can be 500 ml or less, 250 ml or 100 ml or less. Hence the density or dose of the desired cells can be from about $1 \times 10^6$ cells to about $1 \times 10^2$ cells, and in some embodiments can be from about $1 \times 10^8$ cells to about $1 \times 10^{11}$ cells. In some embodiments, cytotoxic cells in these amounts can be utilized for the treatment of cancer in adult humans, compared to about $5 \times 10^6$-$5 \times 10^7$ cells used in mice.

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, and/or increasing the lifespan of a subject with cancer. More generally, these other compositions would be provided in a combined amount effective to kill or inhibit proliferation of the cancer cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

In some embodiments, the present inventive therapy may precede and/or follow the other agent treatment(s) by intervals ranging from minutes to weeks. In embodiments where the other agent and the therapy of the present invention are applied separately to the subject, one would generally ensure that a significant period of time did not expire between each delivery, such that the agent and inventive therapy would still be able to exert an advantageously combined effect on the cell. In such instances, it is contemplated that one may contact the cell with the multiple modalities within about 12-24 hours of each other and, more preferably, within about 6-12 hours of each other. In some situations, it may be desirable to extend the time period for treatment significantly, however, where several days (2, 3, 4, 5, 6 or 7) to several week(s) (1, 2, 3, 4, 5, 6, 7 or 8) lapse between the respective administrations.

It is expected that the treatment cycles would be repeated as necessary. It also is contemplated that various standard therapies, as well as surgical intervention, may be applied in combination with the inventive cell therapy.

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, famesyl-protein tansferase inhibitors, transplatinum, 5-fluorouracil, vincristin, vinblastin and methotrexate, or any analog or derivative variant of the foregoing.

In specific embodiments, chemotherapy for a cancer is employed in conjunction with the methods and compositions of this invention, for example before, during and/or after administration of the methods and compositions invention.

Other agents that cause DNA damage and have been used in cancer treatment include gamma rays, X-rays, and/or the directed delivery of radioisotopes to tumor cells. Other forms of DNA damaging agents are also contemplated such as microwaves and UV-irradiation. It is most likely that all of these agents affect a broad range of damage on DNA, on the precursors of DNA, on the replication and repair of DNA, and/or on the assembly and maintenance of chromosomes. Dosage ranges for X-rays range from daily doses of 50 to 200 roentgens for prolonged periods of time (3 to 4 week), to single doses of 2000 to 6000 roentgens. Dosage ranges for radioisotopes vary widely, and depend on the half-life of the isotope, the strength and type of radiation emitted, and the uptake by the neoplastic cells.

The terms "administered," "contacted," "provided to" and "exposed," when applied to a cell, are used herein to describe the process by which a therapeutic agent is delivered to a target cell and/or is placed in direct juxtaposition with the target cell, e.g., under conditions that facilitate binding of a CAR to a target cancer antigen in and/or on a target cancer cell. In some embodiments, chemotherapy and/or radiation therapy can also be included before, after and/or during the administering, contacting, exposing and/or providing to step to achieve cell killing or stasis. In some embodiments, multiple agents can be delivered to a cell in a combined amount effective to kill the cell or prevent it from dividing.

Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and natural killer (NK) cells.

Immunotherapy could thus be used as part of a combined therapy, in conjunction with the present adaptive cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Nonlimiting examples of common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Immunotherapy for a cancer of this invention may include interleukin-2 (IL-2) or interferon (IFN), for example.

In other embodiments, the secondary treatment can be a gene therapy in which a therapeutic polynucleotide is administered before, after, and/or at the same time as the present invention methods and compositions. A variety of expression products is encompassed within the invention, including inducers of cellular proliferation, inhibitors of cellular proliferation, and/or regulators of programmed cell death.

Approximately 60% of persons with cancer will undergo surgery of some type, which includes preventative, diagnostic or staging, curative and/or palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-Ibeta, MCP-1, RANTES, and other chemokines. It is further contemplated that the upregulation of cell surface receptors or their ligands such as Fas/Fas ligand, DR4 or DR5/TRAIL would potentiate the tumor eradicating abilities of the present invention by establishment of an autocrine or paracrine effect on hyperproliferative cells. Increasing intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Nonlimiting examples of suitable chemotherapeutic agents which may be administered with the antibodies or antigen binding fragments as described herein include daunomycin, cisplatin, verapamil, cytosine arabinoside, aminopterin, democolcine, tamoxifen, Actinomycin D, Alkylating agents (including, without limitation, nitrogen mustards, ethylenimine derivatives, alkyl sulfonates, nitrosoureas and triazenes): Uracil mustard, Chlormethine, Cyclophosphamide (Cytoxan©), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide; Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine, natural products and their derivatives (for example, *vinca* alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-α), Etoposide, and Teniposide; Other anti-proliferative cytotoxic agents are navelbene, CPT-11, anastrazole, letrazole, capecitabine, reloxafine, cyclophosphamide, ifosamide, and droloxafine. Additional anti-proliferative cytotoxic agents include, but are not limited to, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Preferred classes of antiproliferative cytotoxic agents are the EGFR inhibitors, Her-2 inhibitors, CDK inhibitors, and Herceptin® (trastuzumab). (see, e.g., U.S. Pat. Nos. 6,537,988; 6,420,377). Such compounds may be given in accordance with techniques currently known for the administration thereof.

As used herein, the term "purified" does not require absolute purity; rather, it is intended as a relative term. Thus, for example, a purified cell population of cytotoxic cells and/or other effector immune cells is one in which the percentage of isolated cells in a population of cells (e.g., in culture) is more pure than said cells in their natural environment, such as within a human subject. In particular examples, substantially purified populations of cytotoxic cells refers to populations of cytotoxic cells that are at least 50%, 60%, 65%, 70%, 75%, 80%, 90%, 95%, 96%, 97%, 98% or 99% pure. In one embodiment, a substantially purified population of cytotoxic cells is composed of at least about 70%, such as at least about 80%, such as at least about 90% cytotoxic cells or cytotoxic cells. That is, the population of cytotoxic cells includes less than about 20%, such as at least about 10%, of other cells such as non-cytotoxic cells. The purity of a cytotoxic cell population or cytotoxic cells can be measured based on cell surface characteristics (e.g., as measured by fluorescence activated cell sorting) or by cytokine secretion profile (e.g., as measured by an ELISA assay), as compared to a control.

In some embodiments, prior to administration of the cells of this invention to a subject, the subject's immune system, such as T cells, can be non-selectively or selectively depleted, or ablated, by any method known in the art, for example, selective depletion or ablation of T cells or a specific subset of T cells. Exemplary treatments to induce lymphopenia in a subject prior to cell administration can include but are not limited to the administration of chemotherapeutics and/or total body irradiation.

In one embodiment, the subject's immune system is depleted or ablated by the administration of an induction chemotherapy regimen comprising a therapeutically effective amount of etoposide, doxorubicin, vincristine, cyclophosphamide, and prednisone (EPOCH). In another embodiment, fludarabine can also be administered to improve the depletion of T cells.

Additionally provided herein are compositions, e.g., for use in the methods of the present invention.

Thus, another aspect of the invention relates to a composition comprising: (a) a first antibody or fragment thereof comprising a targeting ligand and a first antigen binding portion, wherein the first antigen binding portion binds a first cancer cell antigen (e.g., a first antibody or fragment thereof of the present invention); and/or (b) a cytotoxic cell comprising a targeting agent specific for the targeting ligand, wherein the targeting ligand and the targeting agent comprise a bio-orthogonal ligation pair (e.g., a cytotoxic cell of the present invention).

In some embodiments, a composition of the present invention may further comprise a second and/or third antibody or fragment thereof that is each different from the first antibody or fragment thereof, each of the second and/or third antibody or fragment thereof comprising the same targeting ligand as the first antibody or fragment thereof and a second and/or third antigen binding portion (e.g., HER2, EGFR, CD19, CD20, CD45, CD16, HLA-DR, alpha-4 integrin, etc.) that is different from the first antigen binding portion of the first antibody or fragment thereof.

In some embodiments, the cytotoxic cell of the invention is isolated. As used herein, an "isolated" cell is a cell that has been partially or completely separated from other components with which it is normally associated in nature. For example, an isolated cell can be a cell in culture medium and/or a cell in a pharmaceutically acceptable carrier.

In some embodiments, the cytotoxic cell of the invention is purified.

In some embodiments, a composition of the present invention may further comprise a pharmaceutically acceptable carrier (i.e., a pharmaceutical composition).

In some embodiments, the present invention provides a pharmaceutical composition comprising a first, second, third, or more antibody or fragment thereof and/or cytotoxic cell of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

The compositions of the present invention can also include other medicinal agents, pharmaceutical agents, carriers, diluents, immunostimulatory cytokines, etc.

Injectables can be prepared in conventional forms, either as liquid solutions or suspensions, solid forms suitable for solution or suspension in liquid prior to injection, or as emulsions.

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharm. Res.* 3:318 (1986)) and typically take the form of an optionally buffered aqueous solution of the composition of this invention. Suitable formulations can comprise citrate or bis\ris buffer (pH 6) or ethanol/water and can contain from 0.1 to 0.2M active ingredient.

The compositions disclosed herein may be administered to the lungs of a subject by any suitable means, for example, by administering an aerosol suspension of respirable particles comprised of the compositions, which the subject inhales. The respirable particles may be liquid or solid. Aerosols of liquid particles comprising the compositions may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compositions of the invention may likewise be produced with any solid particulate medicament aerosol generator, by techniques known in the pharmaceutical art.

The compositions of the present invention may be of use in any method in which they would be beneficial, such as but not limited to, use of the cytotoxic cell and/or the antibody or fragment thereof of the invention in inducing cytotoxicity in a cancer cell, use of the cytotoxic cell and/or the antibody or fragment thereof of the invention in delivering a cytotoxic cell to a cancer cell in a subject, and/or use of the cytotoxic cell and/or the antibody or fragment thereof of the invention in treating cancer.

Another aspect of the present invention provides for methods of preparation of a medicament for use comprising the cytotoxic cell and/or the antibody or fragment thereof of the invention.

The present invention further provides a kit comprising one or more compositions of this invention. It would be well understood by one of ordinary skill in the art that the kit of this invention can comprise one or more containers and/or receptacles to hold the reagents (e.g., antibodies, cells, etc.) of the kit, along with appropriate buffers and/or diluents and/or other solutions and directions for using the kit, as would be well known in the art. Such kits can further comprise adjuvants and/or other immunostimulatory or immunomodulating agents, as are well known in the art.

Accordingly, further provided herein is a kit comprising the cytotoxic cell and/or the antibody or fragment thereof of the invention and instructions for use.

Methods of Making.

Additionally provided herein are methods of making the antibodies or fragments thereof of the present invention and/or the cytotoxic cells of the present invention.

Thus, one aspect of the invention provides a method of making an antibody or fragment thereof of the present invention (e.g., for use in the methods of the present invention), comprising: (a) incubating an unmodified antibody or fragment thereof with a first reaction agent comprising a functional group (e.g., DBCO, Tz, etc.) to produce an antibody or fragment thereof expressing the functional group (e.g., Ab-DBCO, Ab-Tz, etc.), wherein the functional group is the targeting ligand, thereby modifying the antibody or fragment thereof to express the targeting ligand.

Another aspect of the invention provides a method of making cytotoxic cell (e.g., for use in the methods of the present invention), comprising: incubating an unmodified cytotoxic cell with a first reaction agent comprising a functional group (e.g., a glycosylation agent) to produce a cytotoxic cell expressing the functional group on the surface of the cell, thereby modifying the cytotoxic cell to express the functional group on the surface of the cytotoxic cell.

In some embodiments, the methods of making a cytotoxic cell of the present invention may further comprise incubating the functional group-expressing cytotoxic cell with a second reaction agent which produces a targeting agent upon reaction (e.g., dibenzylcyclooctyne-trans-cyclooctene (DBCO-TCO), which produces TCO upon reaction) under conditions whereby the functional group on the surface of the cytotoxic cell is replaced with the targeting agent of the second reaction to produce a cytotoxic cell expressing the targeting agent, thereby modifying the cytotoxic cell to express the targeting agent on the surface of the cytotoxic cell.

The unmodified cytotoxic cell of the present invention may be any mammalian effector cell capable of inducing cell death in a target cell, such as but not limited to a mammalian innate and/or adaptive immune effector cell. In some embodiments, the unmodified cytotoxic cell may be a natural killer (NK) cell, a T cell (e.g., T helper cell, T cytotoxic cell (CTL), T gamma delta (γδ) cell, etc.), macrophage, or dendritic cell. In some embodiments, the unmodified cytotoxic cell may be an NK cell. In some embodiments, the unmodified cytotoxic cell may be a CTL. In some embodiments, the unmodified cytotoxic cell may be a macrophage. In some embodiments, the unmodified cytotoxic cell may be a dendritic cell.

A first and/or a second reaction agent of the present invention may comprise any reaction agent(s) as needed to attach the functional group (e.g., wherein the functional group is the targeting ligand and/or wherein the functional group is used as a first step in a two-step process whereby a second agent contacts the functional group to attach a targeting agent) to the unmodified cytotoxic cell, in either a single step and/or a two-step process. Non-limiting examples of a first reaction agent comprising a functional group of use in the present invention include glycosylation agents such as N-azidoacetylmannosamine tetraacylated (ManNAz) and/or N-Cyclopropeneacetylatedmannosamine-tetraacylated (ManNCyoc). Non-limiting examples of a second reaction agent of the present invention include dibenzylcyclooctyne-trans-cyclooctene (DBCO-TCO) (e.g., wherein the targeting ligand produced by the process involving the second agent is trans-cyclooctene (TCO)).

In some embodiments of the methods of the methods of the present invention, the targeting ligand and the targeting agent specific for the targeting ligand may comprise any pair which bind together (e.g., biotin and streptavidin). In some embodiments, the targeting ligand and the targeting agent specific for the targeting ligand may comprise a bio-orthogonal ligation pair (e.g., tetrazine and trans-cyclooctene). In some embodiments, the targeting ligand and the targeting agent may bind via a bio-orthogonal 'click' chemistry reaction, such as but not limited to an inverse-demand Diels-Alder cycloaddition (IEDDA) reaction or a strain-promoted azide-alkyne cycloaddition (SPAAC) reaction.

In some embodiments, the present invention may be as defined in any one of the following numbered paragraphs.

1. A method of inducing cytotoxicity in a cancer cell, the method comprising: (a) contacting the cancer cell with a first antibody or fragment thereof, wherein the first antibody or fragment thereof comprises a first antigen binding portion and a targeting ligand and wherein the cancer cell comprises a first antigen on the surface of the cancer cell, under conditions whereby the first antigen binding portion of the first antibody or fragment thereof binds the first antigen on the surface of the cancer cell; and (b) contacting the cancer cell of step (a) with a cytotoxic cell comprising a targeting agent specific for the targeting ligand, under conditions whereby the targeting agent binds the targeting ligand (e.g., via an inverse-demand Diels-Alder cycloaddition (IEDDA) reaction, e.g., via a strain-promoted azide-alkyne cycloaddition (SPAAC) reaction), thereby inducing cytotoxicity in the cancer cell.

2. A method of delivering a cytotoxic cell to a cancer cell, the method comprising: (a) contacting the cancer cell with a first antibody or fragment thereof, wherein the first antibody or fragment thereof comprises a first antigen binding portion and a targeting ligand and wherein the cancer cell comprises a first antigen on the surface of the cancer cell, wherein the first antigen binding portion of the first antibody or fragment thereof binds the first antigen on the surface of the cancer cell; and (b) contacting the cancer cell of step (a) with a cytotoxic cell comprising a targeting agent specific for the targeting ligand, wherein the targeting agent binds the targeting ligand (e.g., via an inverse-demand Diels-Alder cycloaddition (IEDDA) reaction, e.g., via a strain-promoted azide-alkyne cycloaddition (SPAAC) reaction), thereby delivering the cytotoxic cell to the cancer.

3. The method of paragraph 1 or 2, wherein the cancer cell is in a subject having, suspected of having, or at risk of having cancer.

4. A method of treating cancer in a subject in need thereof, comprising: (a) administering to the subject an effective amount of a first antibody or fragment thereof, wherein the first antibody or fragment thereof comprises a first antigen binding portion specific for a first cancer antigen and a targeting ligand, and wherein the cancer comprises the first cancer antigen specific for the first antigen binding portion (e.g., on the surface one or more cancer cells), wherein the first antigen binding portion of the first antibody or fragment thereof binds the first cancer antigen (e.g., on the surface of the one or more cancer cells); and (b) administering to the subject of (a) an effective amount of a cytotoxic cell comprising a targeting agent specific for the targeting ligand, wherein the targeting agent binds the targeting ligand (e.g., via an inverse-demand Diels-Alder cycloaddition (IEDDA) reaction, e.g., via a strain-promoted azide-alkyne cycloaddition (SPAAC) reaction), thereby treating the cancer in the subject.

5. The method of any one of paragraphs 1-4, further comprising contacting with or administering a second or more antibody or fragment thereof different from said first antibody or fragment thereof, wherein each of the second or more antibody or fragment thereof comprises the same targeting ligand (e.g., each comprising TZ) as said first antibody or fragment thereof and a second or more antigen binding portion (e.g., HER2, EGFR, CD19, CD20, CD45, CD16, etc.) that is different from the first antigen binding portion of said first antibody or fragment thereof.

6. The method of any one of paragraphs 1-5, further comprising contacting with or administering a third antibody or fragment thereof different from said first antibody or fragment thereof and said second antibody or fragment thereof, wherein the third antibody or fragment thereof comprises the same targeting ligand (e.g., each comprising TZ) as the first and the second antibody or fragment thereof and a third antigen binding portion (e.g., HER2, EGFR, CD19, CD20, CD45, CD16, etc.) that is different from the first and said second antigen binding portion of said first and said second antibody or fragment thereof.

7. The method of any one of paragraphs 1-6, wherein the cytotoxic cell is a natural killer (NK) cell, cytotoxic T lymphocyte (CTL), macrophage, or dendritic cell.

8. The method of paragraph 7, wherein the cytotoxic cell is an NK cell.

9. The method of any one of paragraphs 1-8, wherein the cytotoxic cell comprises a cytotoxic cell line (e.g., NK92 cell line) modified to express the targeting agent.

10. The method of any one of paragraphs 1-8, wherein the cytotoxic cell comprises a cytotoxic cell from a donor (e.g., from the subject; e.g., from a donor unrelated (e.g., allogeneic) to the subject) modified ex vivo to express the targeting agent.

11. The method of any one of paragraphs 1-10, wherein the antibody or fragment thereof (e.g., the first, second, or more antibody or fragment thereof) is selected from the group consisting of a monoclonal antibody, a Fab fragment, a Fab'-SH fragment, a FV fragment, a scFV fragment, a (Fab')$_2$ fragment, an Fc-fusion protein, an affibody, and any combination thereof.

12. The method of any one of paragraphs 1-11, wherein the targeting agent and the targeting ligand comprise a bio-orthogonal ligation pair.

13. The method of any one of paragraphs 1-12, wherein the targeting ligand is selected from the group consisting of streptavidin (SA), dibenzylcyclooctyne (DBCO), tetrazine, bicyclononyne (BCN), and any combination thereof.

14. The method of any one of paragraphs 1-13, wherein the targeting agent is selected from the group consisting of biotin, azide (Az), cyclopropene (Cp), trans-cyclooctene (TCO), and any combination thereof.

15. The method of any one of paragraphs 1-14, wherein the cancer antigen (e.g., the first, second, or more cancer antigen) is HER2, EGFR, CD19, CD20, CD45, CD16, HLA-DR, alpha-4 integrin, or any combination thereof.

16. The method of any one of paragraphs 1-15, wherein the antigen binding portion (e.g., the first, second, or more antigen binding portion) is an anti-HER2, EGFR, CD19, CD16, HLA-DR or alpha-4 integrin binding portion, or any combination thereof.

17. The method of any one of paragraphs 2-16, wherein the cancer is breast cancer (e.g., BRCA+, HER2+, triple negative, etc.), lung cancer, lymphoma, colon cancer, prostate cancer, leukemia, multiple myeloma, or any combination thereof.

18. The method of any one of paragraphs 4-17, wherein the administering step is via a route selected from the group consisting of intravenous, intramuscular, subcutaneous, topical, oral, transdermal, intraperitoneal, intrathecal, intraventricular, intravitreal, intraocular, intraorbital, intranasal, by implantation, by inhalation, by intratumoral, and any combination thereof.

19. The method of any one of paragraphs 3-18, wherein the subject is a human.

20. A kit comprising the cytotoxic cell and/or the antibody or fragment thereof of any one of paragraphs 1-19 and instructions for use.

21. A method of making the antibody or fragment thereof used in the method of any one of paragraphs 1-19, comprising: (a) incubating an unmodified antibody or fragment thereof with a first reaction agent comprising a functional group (e.g., DBCO, Tz, etc.) to produce an antibody or fragment thereof expressing the functional group (e.g., Ab-DBCO, Ab-Tz, etc.), wherein the functional group is the targeting ligand of any one of paragraphs 1-19, thereby modifying the antibody or fragment thereof to express the targeting ligand.

22. A method of making cytotoxic cell used in the method of any one of paragraphs 1-19, comprising: incubating an unmodified cytotoxic cell with a first reaction agent comprising a functional group (e.g., a glycosylation agent, e.g., ManNAz, ManNCyoc, ManANz, etc.) to produce a cytotoxic cell expressing the functional group on the surface of the cell (e.g., NK-Az, NK-Cp, NK-Nz), thereby modifying the cytotoxic cell to express the functional group on the surface of the cytotoxic cell.

23. The method of paragraph 22, wherein the functional group is the targeting agent of any one of paragraphs 1-19 (e.g., Az, Cp, Tz).

24. The method of paragraph 22, further comprising: incubating the functional group-expressing cytotoxic cell with a second reaction agent which produces a targeting agent upon reaction (e.g., dibenzylcyclooctyne-trans-cyclooctene (DBCO-TCO), which produces TCO upon reaction) under conditions whereby the functional group on the surface of the cytotoxic cell is replaced with the targeting agent of the second reaction to produce a cytotoxic cell expressing the targeting agent, thereby modifying the cytotoxic cell to express the targeting agent on the surface of the cytotoxic cell.

25. The method of any one of paragraphs 22-24, wherein the unmodified cytotoxic cell is a cytotoxic cell line (e.g., NK92 cell line).

26. The method of any one of paragraphs 22-24, wherein the unmodified cytotoxic cell is an ex vivo cytotoxic cell from a donor (e.g., from the subject, e.g., from a donor unrelated to the subject).

27. The method of any one of paragraphs 24-27, wherein the second reaction agent and the targeting agent are DBCO-TCO and TCO.

28. The method of any one of paragraphs 22-27, wherein the targeting ligand and the targeting agent comprise a bio-orthogonal ligation pair.

29. The method of paragraph 28, wherein the targeting ligand and the targeting agent bind via an inverse-demand Diels-Alder cycloaddition (IEDDA) reaction or a strain-promoted azide-alkyne cycloaddition (SPAAC) reaction.

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1: General Strategy Overview

A pretargeting platform is applied using bioorthogonal 'click' chemistry to recruit NK cells to kill the target cancer cell. In this approach, NK cells are glycosylated with mannose azide (ManNAz) followed by dibenzylcyclooctyne-trans-cyclooctene (DBCO-TCO) to express TCO on the surface (TCO-NK cells). In a separate preparation, antibodies (Abs) are functionalized with tetrazine (TZ).

FIG. 1 depicts the two-step process wherein 1) the target cancer cell is primed with Ab-TZ to coat the surface of the target tumor cell with TZ, and 2) TCO-NK cells are provided which bind specifically to the target tumor cell. Upon contact with the target tumor cell, TCO on the surface of the NK cells undergoes a rapid IEDDA reaction (reaction rate up to $10^5$ $M^{-1}s^{-1}$) with TZ on the surface of the tumor cell via click chemistry. The high-affinity chemical bond between TCO-TZ anchors NK cell on the target tumor cells and allows enhanced ADCC, resulting in effective tumor cell killing.

Figure 2:
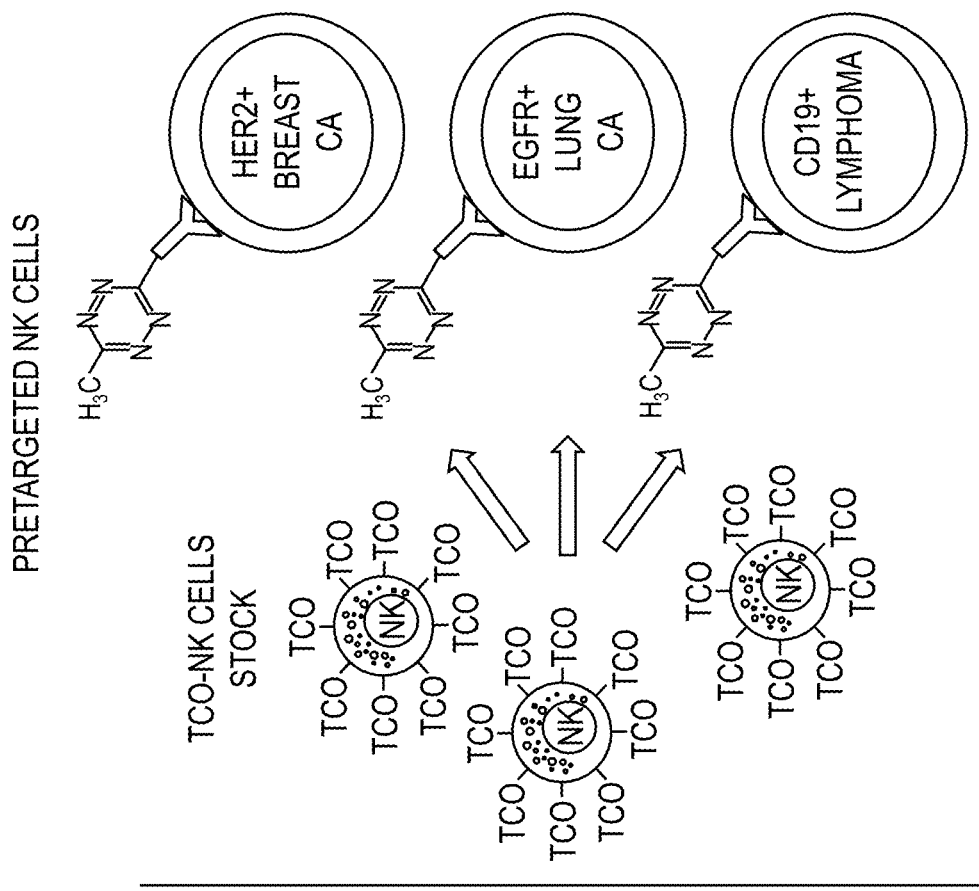
FIG. 2 shows a cartoon comparing chimeric antigen receptor (CAR)-T therapy and pretargeted NK-cell therapy of the present invention.
Figure 2:
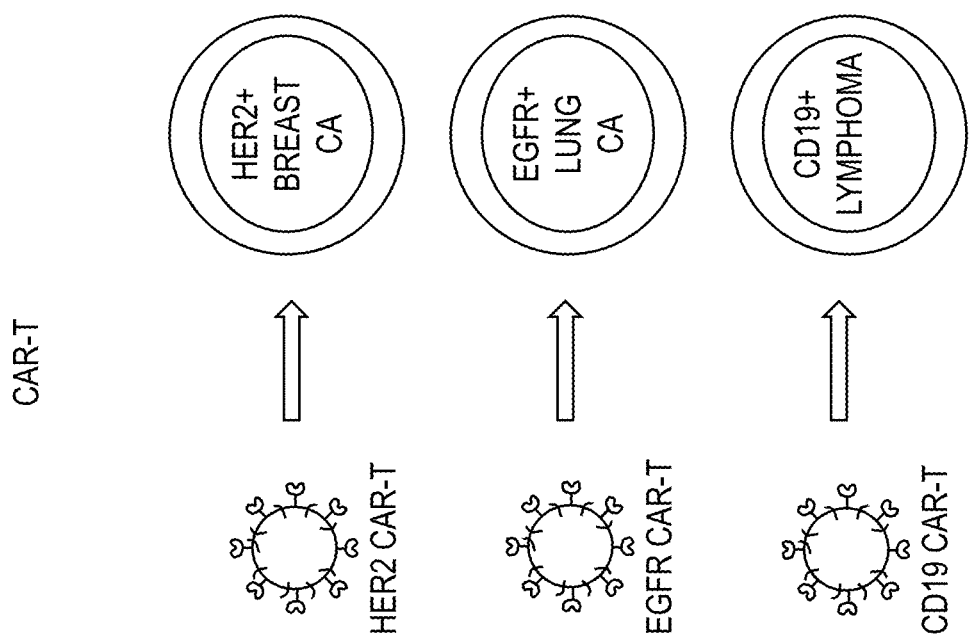
Figure 3:
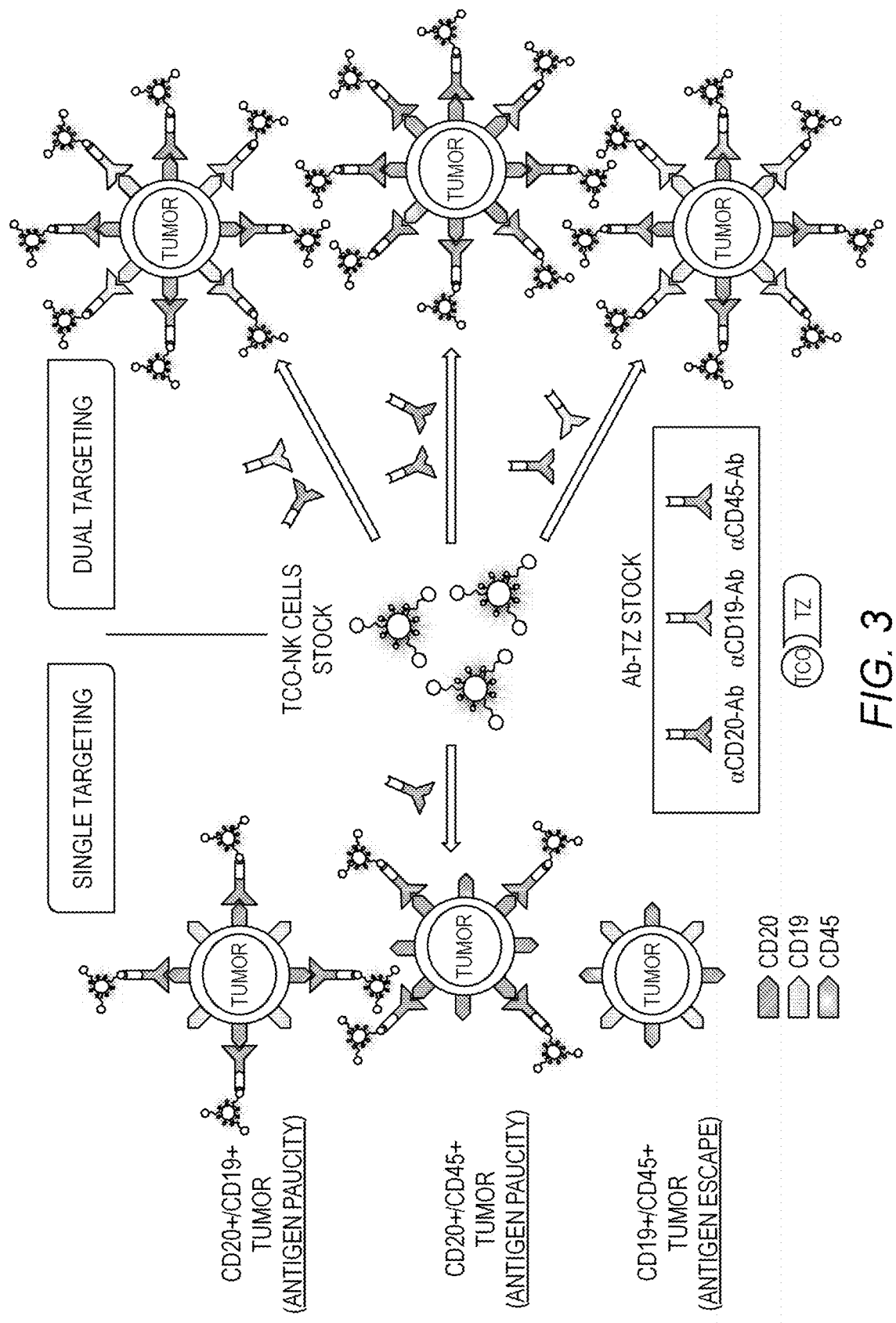
FIG. 3 shows a cartoon comparing single tumor antigen targeting (e.g., CAR-T and CAR-NK) susceptible to treatment resistance via antigen paucity and/or antigen escape, as compared to the present invention pretargeted NK-cell therapy allowing for dual or triple targeting of tumor antigens by 'priming' the target tumor with multiple antibodies.

Pretargeted NK cells according to this protocol allow "off-the-shelf" cellular immunotherapy since the same NK cells may be used for multiple tumor types as long as the target tumor is primed with an appropriate antibody comprising a cancer antigen binding portion (FIG. 2). This pretargeted NK cell therapy of this protocol overcomes antigen paucity and antigen escape by targeting multiple tumor-specific antigens at the same time by priming the target tumor cells with multiple Abs (FIG. 3).

Example 2: Proof of Principle Model Using DBCO-TCO and TZ

Figure 4:
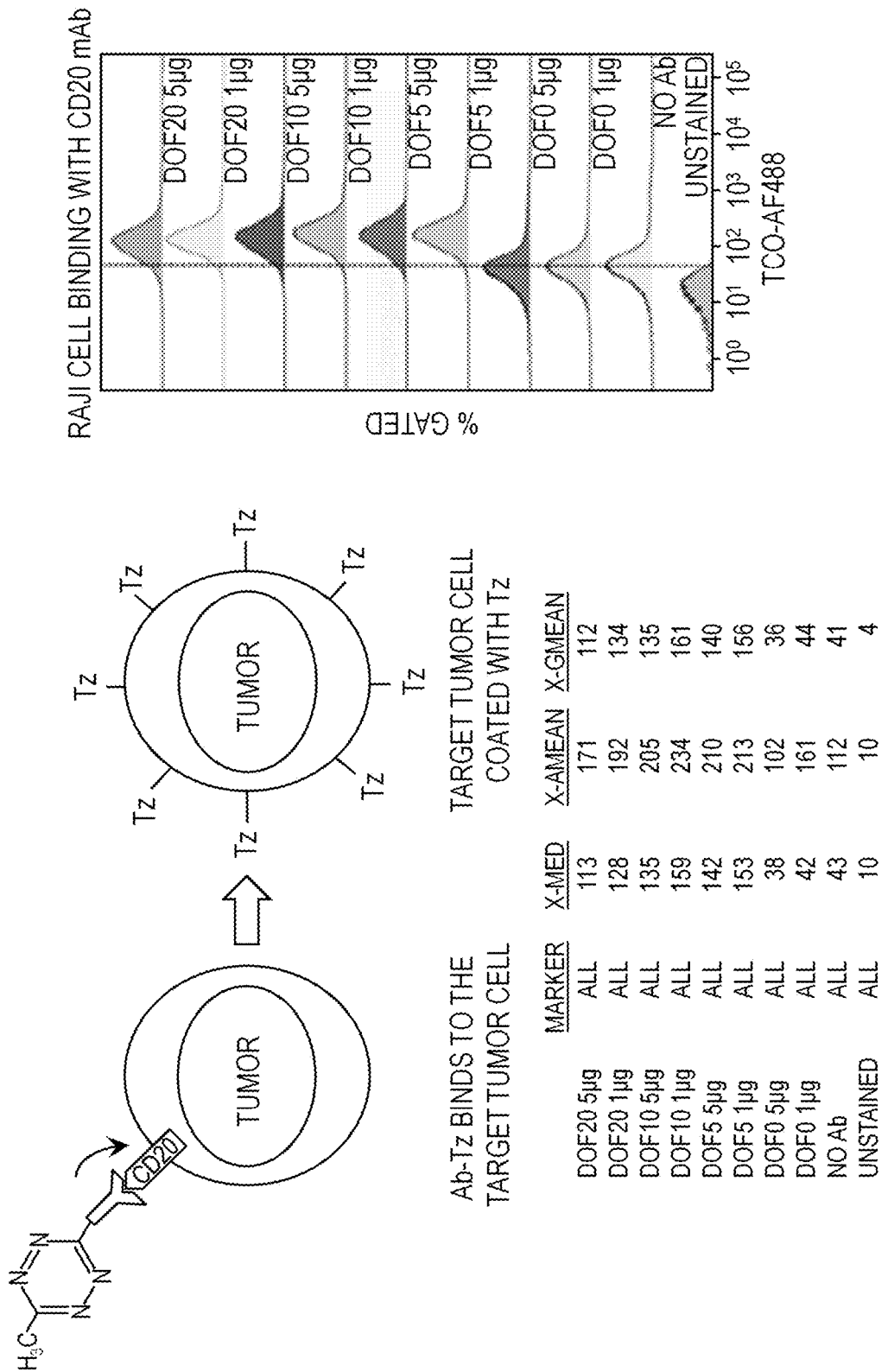
FIG. 4 shows a cartoon (left) modeling anti-CD20 Ab-TZ binding to the target tumor cell (CD20+ Raji), and Flow cytometry data (right) showing fluorescently labeled TCO binds to Tz on the surface of the target tumor cells.

First antibodies were functionalized with DBCO (for binding with AZ-NK-cells) or Tz (for binding with TCO-NK-cells). Anti-CD20 Abs were reacted with polyethylene glycol (PEG)-DBCO or PEG-TZ at various ratios for conjugation with DBCO or TZ. Ultraviolet-visible spectrometer (UV-vis) confirmed the incorporation of DBCO or TZ to the Abs. Flow cytometric analysis confirmed the binding of Ab-DBCO or Ab-Tz to the target tumor (Raji) cells (FIG. 4).

Figure 5:
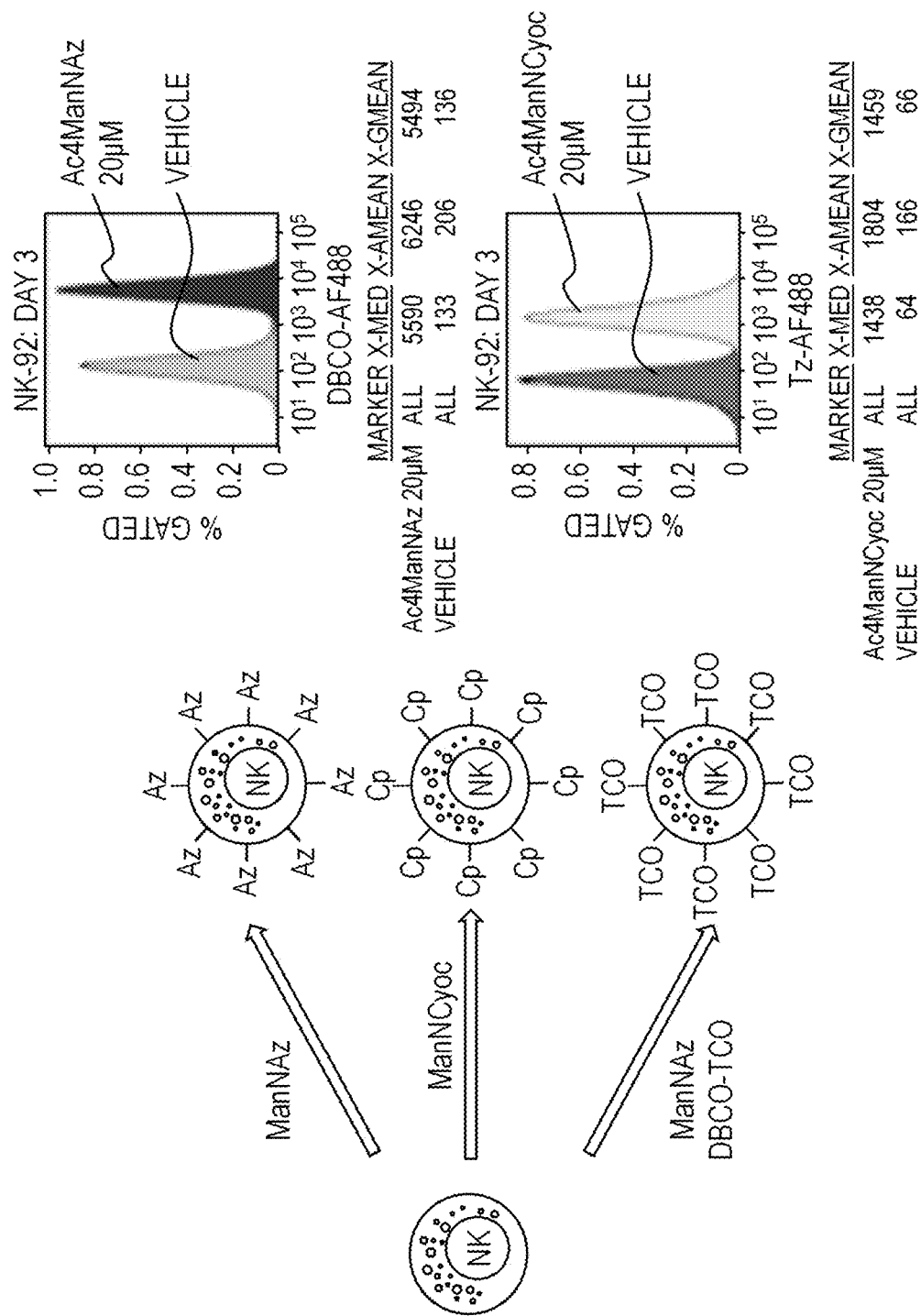
FIG. 5 shows a cartoon (left) of NK cells glycoengineered via incubation with ManNAz, ManNCyoc, or ManANz followed by DBCO-TCO, and Flow cytometry data (right) confirming NK cells expressing Az, Cp, or TCO on the surface.

Next, NK cells were functionalized in a separate preparation. NK cells were glycoengineered by incubating with ManNAz (for binding with Ab-DBCO) or N-Cycloprope-neacetylatedmannosamine-tetraacylated (ManNCyoc; for binding with Ab-Tz) for 48 hours. The incorporation of Az, cyclopropene (Cp), or TCO was confirmed by flow cytometry (FIG. 5).

Figure 6:
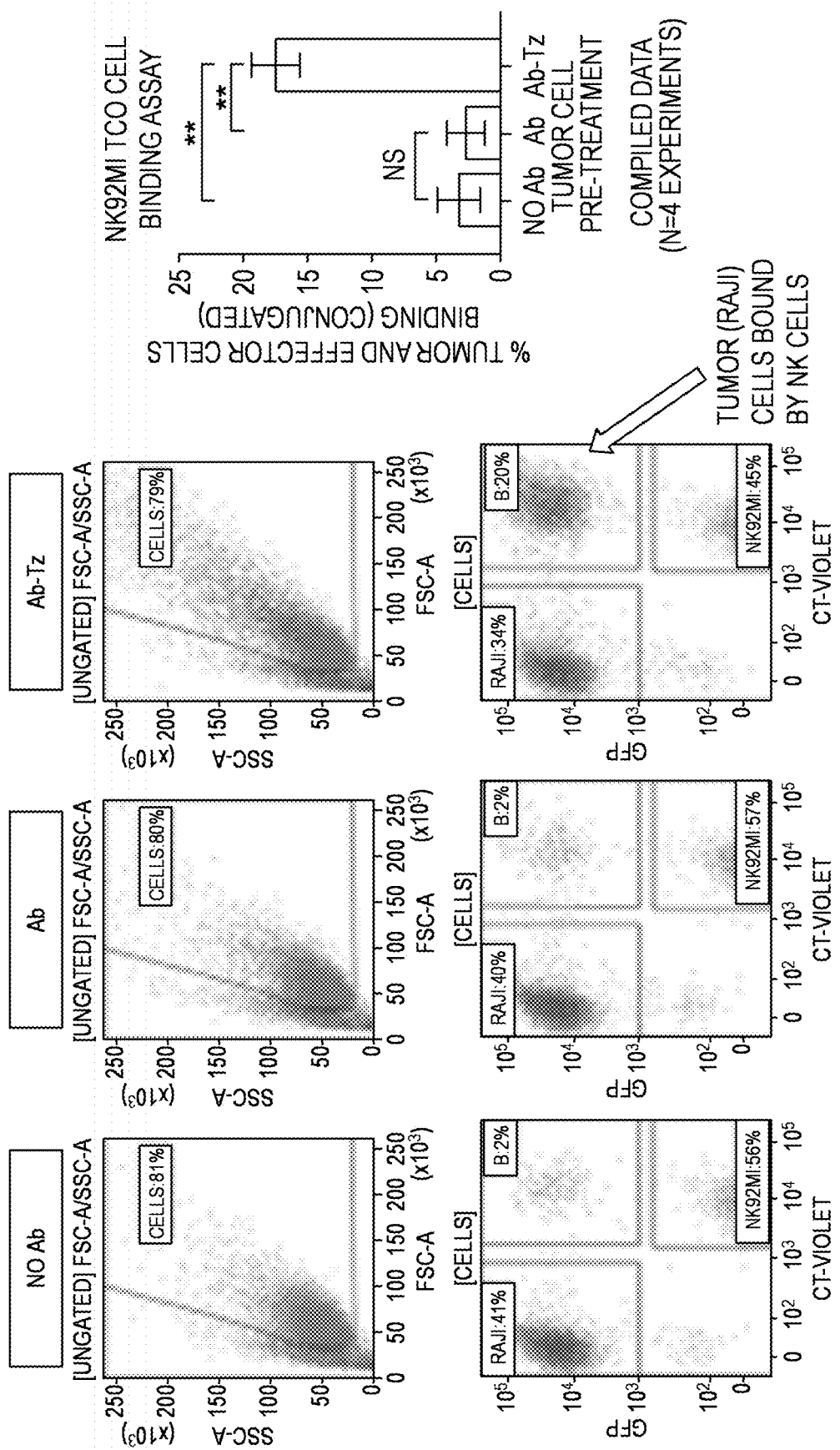
FIG. 6 shows data plots of flow cytometry (left) and a bar graph (right) quantifying binding activity to NK92 cells. The flow cytometry data examined NK cells glycoengineered via incubation with ManNAz, ManNCyoc, or ManANz followed by DBCO-TCO, and showed NK cells expressing Az, Cp, or TCO on the surface.
Figure 7:
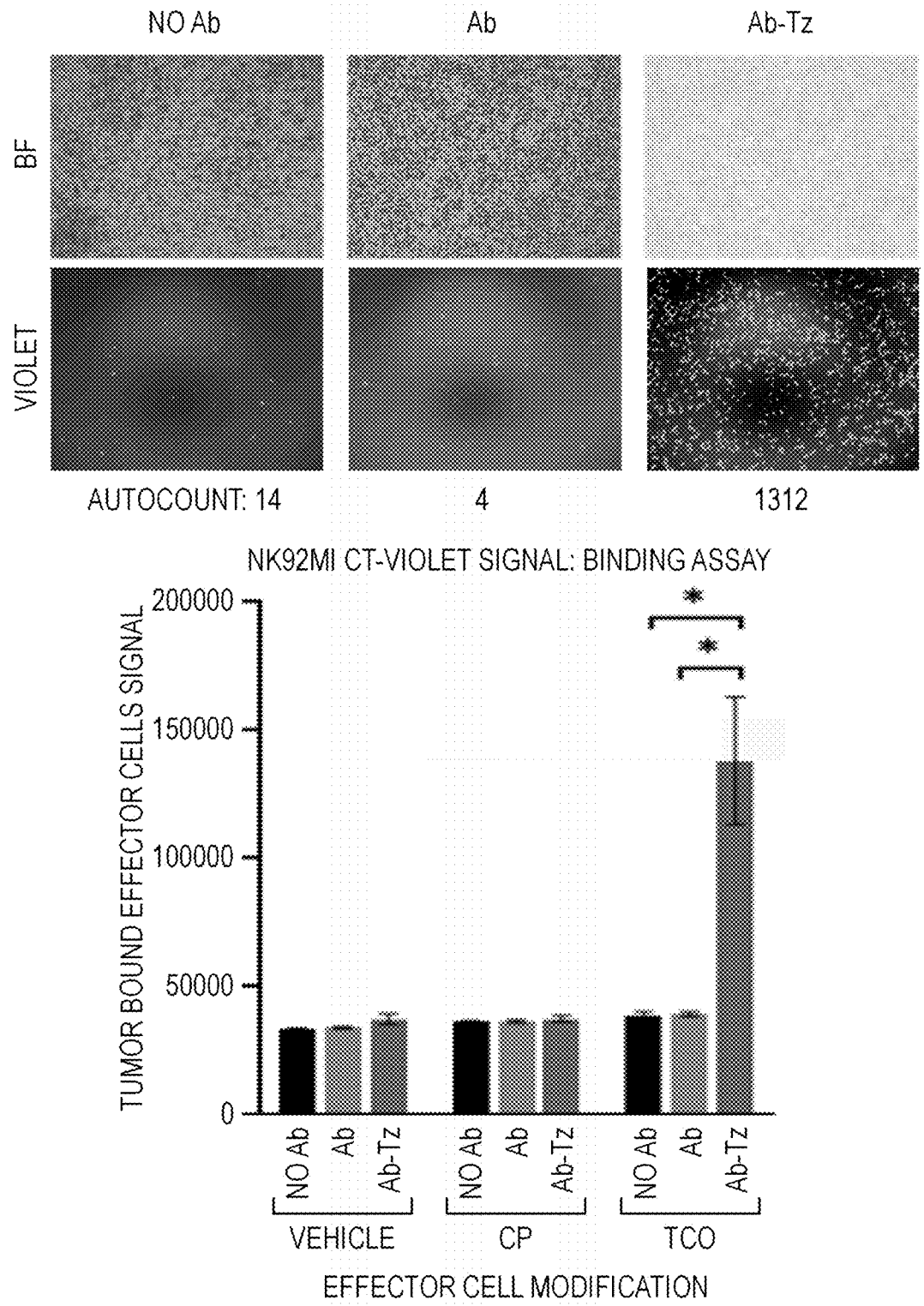
FIG. 7 shows microscopy images (left) and a bar graph (right) of cell adhesion assays demonstrating TCO-NK cells binding to the tumor cell layer comprised with CD20+ Raji cells 'primed' with Ab-Tz.

Binding of Ab-DBCO to Az-NK cells as well as binding of Ab-Tz to Cp-NK or TCO-NK cells was evaluated using flow cytometry and cell adhesion assays. The combination of Ab-Tz and TCO-NK cells demonstrated the most effective binding compared to other formulations (FIGS. 6 and 7).

To evaluate the effect of pretargeted delivery on ADCC, Jurkat-Lucia NFAT-CD16 cells (JL-CD16) were used as a surrogate for CD16+NK cells. Upon the binding of CD16 to the target cells, lucia luciferase reporter gene gets expressed by JL-CD16 cells. Therefore, the degree of ADCC can be measured by the level of lucia luciferase activity.

Figure 8:
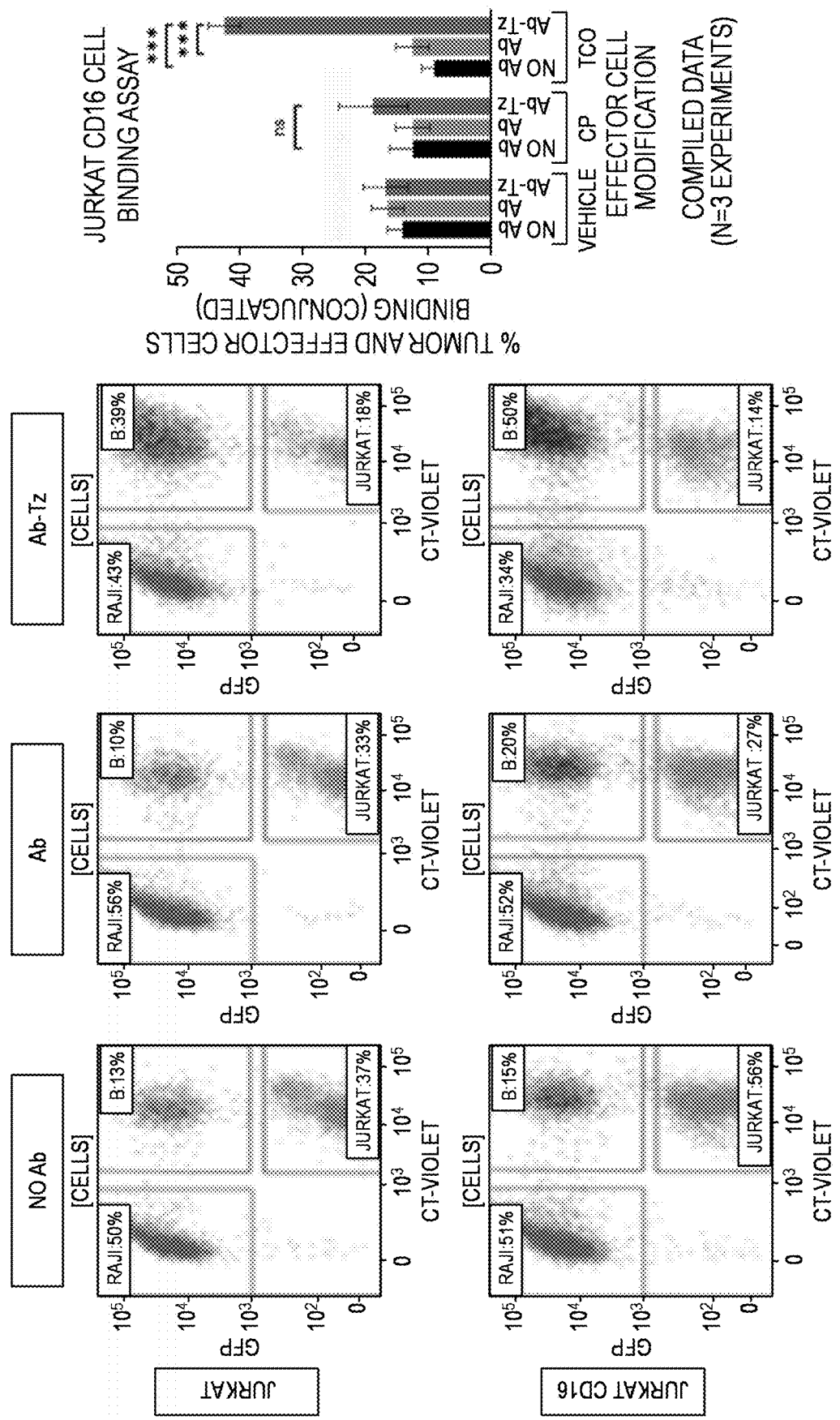
FIG. 8 shows flow cytometry plots (left) and a bar graph (right) of JL-CD16 cells glycoengineered via incubation with ManANz followed by DBCO-TCO. Flow cytometry showed TCO-JL-CD16 cells were binding to the target tumor (Raji cells).
Figure 9:
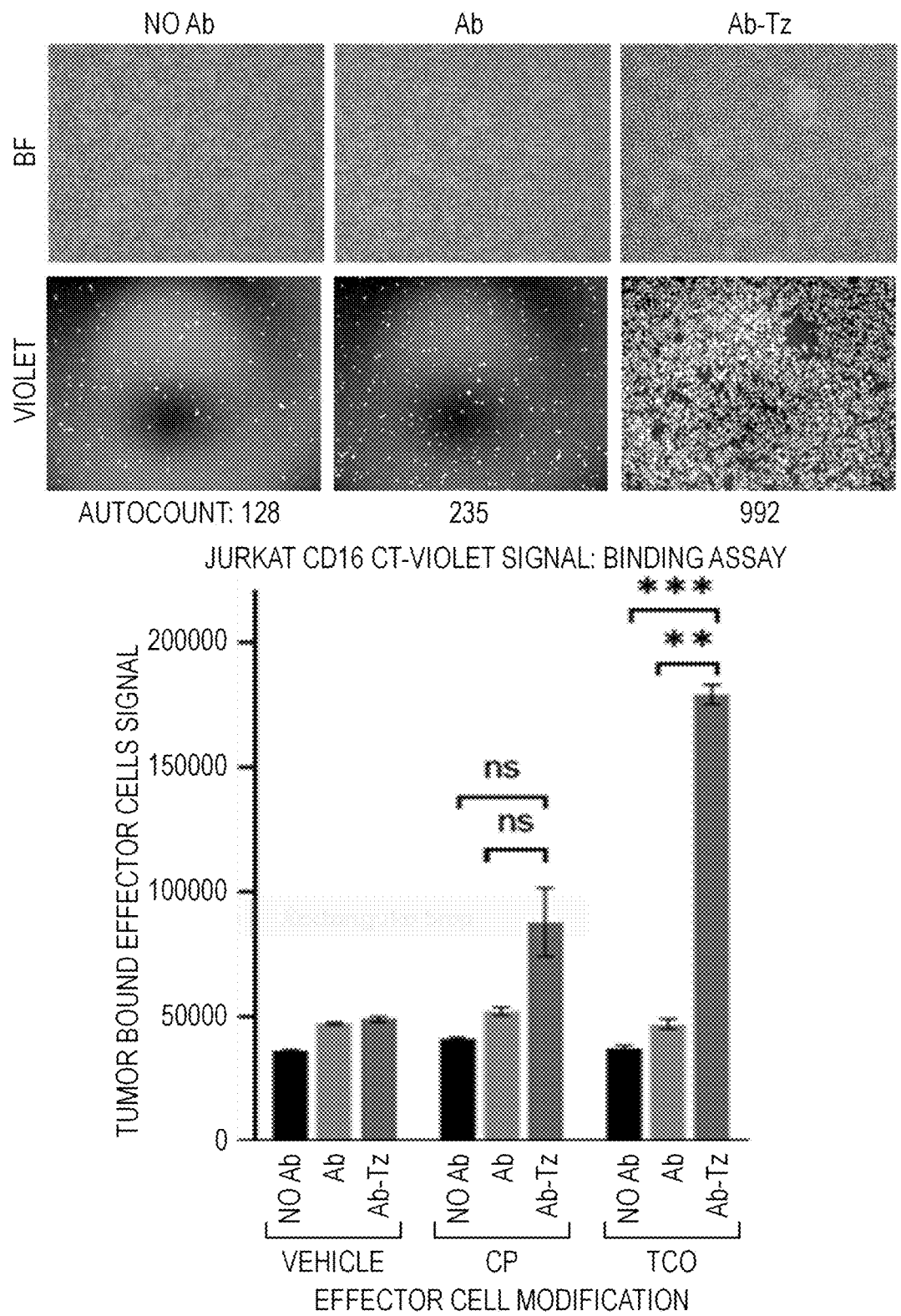
FIG. 9 shows microscopy images (left) and a bar graph (right) of cell adhesion assays demonstrating TCO-NK cells binding to the tumor cell layer comprised with CD20+ Raji cells 'primed' with Ab-Tz.
Figure 10:
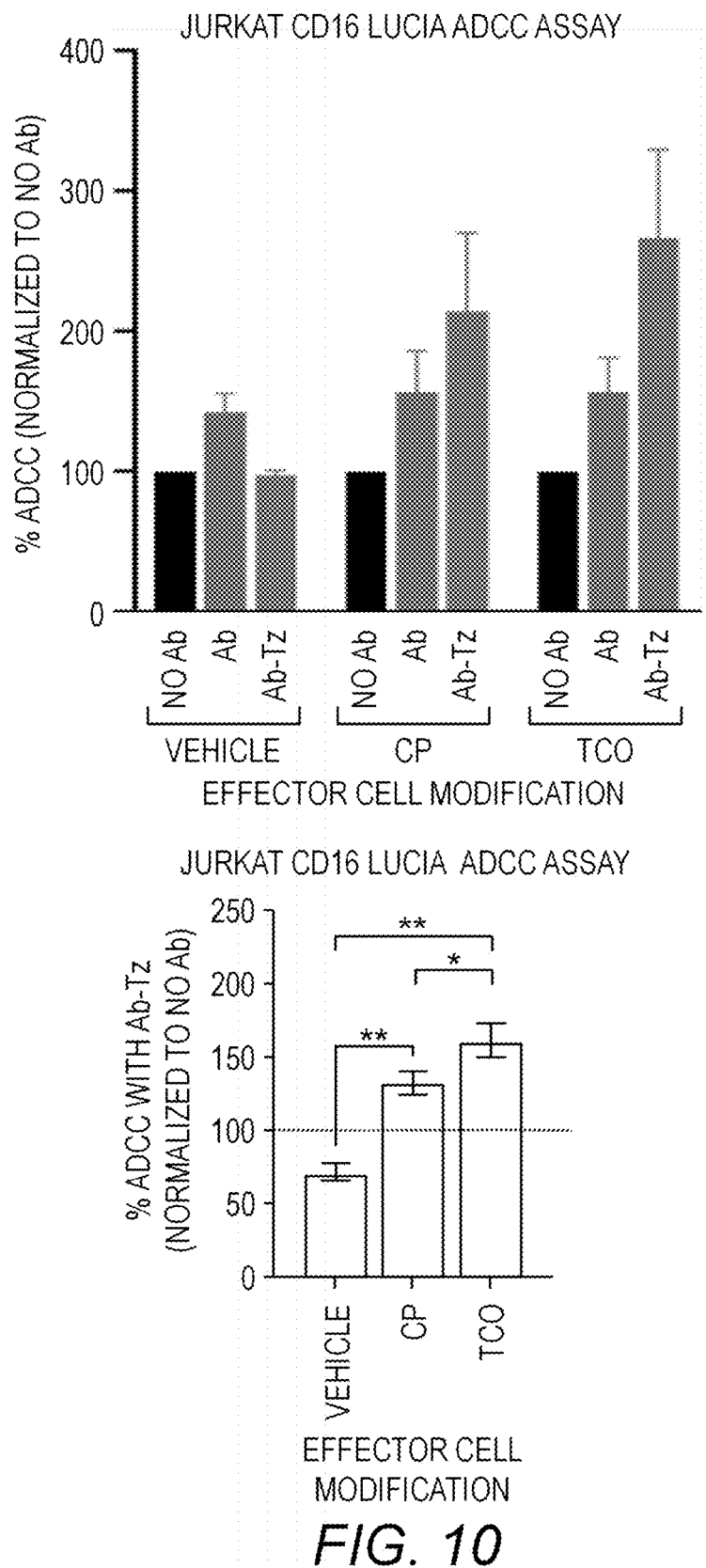
FIG. 10 shows bar graphs of TCO-Jurkat-CD16 cells activating ADCC upon binding to Raji lymphoma cells. Pretargeted immunotherapy increases ADCC by >2-fold.

The specific binding of JL-CD16 cells to Raji cells 'primed with Ab-Tz' when glycosylated with ManNAz followed by DBCO-TCO was confirmed (FIGS. 8 and 9). ADCC activity levels were then measured, which showed that pretargeted delivery of JL-CD16 cells to the target tumor cells increased ADCC by more than 2-fold (FIG. 10).

The pretargeting platform disclosed herein can be designed in various different permutations involving binding couples, such as streptavidin (SA)/biotin, DBCO/Az, Tz/Cp, and Tz/TCO. SA/biotin is limited by immunogenicity of SA and endogenous biotin, and novel binding couples utilizing bioorthogonal 'click' chemistry have emerged as the next generation method for pretargeting platform. DBCO/Az, Tz/Cp, and Tz/TCO were compared and it was found that Tz/TCO was the most effective in recruiting NK cells to the target cancer cell.

While not wishing to be bound to theory, Tz/TCO may be superior to DBCO/Az as the IEDDA reaction using Tz/TCO has a significantly faster reaction rate than SPAAC using DBCO/Az ($\sim 10^5$ $M^{-1}s^{-1}$ vs. $\sim 1$ $M^{-1}s^{-1}$, respectively). Although both pairs use the same IEDDA click chemistry, Tz/TCO pair binding was significantly more effective than Tz/Cp in locking NK cells to the target tumor cells.

Example 3: In Vivo Application

Figure 11:
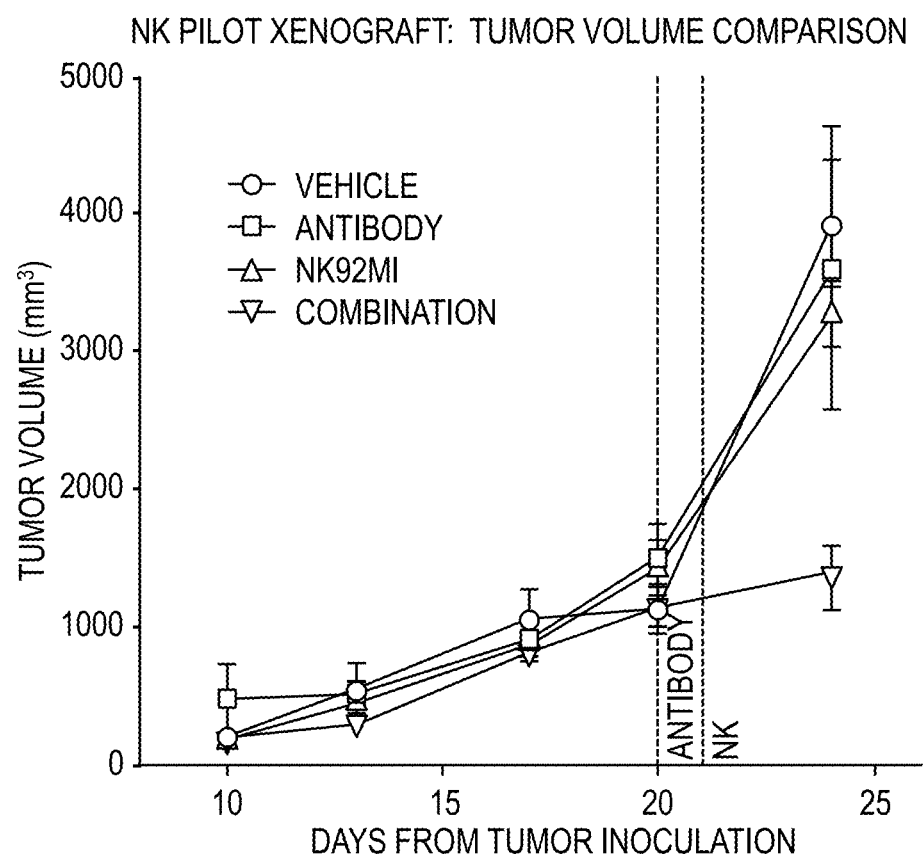
FIG. 11 shows a data graph measuring tumor volume ($mm^3$) over time (days post tumor inoculation) in four groups in an in vivo xenograft model. Groups shown include vehicle, antibody treatment alone ("Antibody"), non-targeted (no pre-antibody) NK cell therapy ("NK92MI"), and combination pretargeted NK cell therapy such as described herein ("Combination").

An in vivo experiment was performed using a murine lymphoma xenograft model. Pretargeted NK cell therapy as described herein was administered and associated with >50% reduction in tumor volume within 5 days of therapy. Treatment groups were compared with negative controls, including antibody treatment only and nontargeted NK cell therapy. Each treated animal received NK cells at $5 \times 10^6$ in PBS. Data from this experiment are shown in FIG. 11.

The foregoing is illustrative of the present invention, and is not to be construed as limiting thereof. The invention is defined by the following claims, with equivalents of the claims to be included therein.

That which is claimed is:

1. A method of inducing cytotoxicity in a cancer cell in a subject having, suspected of having, or at risk of having cancer, the method comprising:
    (a) contacting the cancer cell with a first antibody or fragment thereof, wherein the first antibody or fragment thereof comprises a first antigen binding portion and a targeting ligand and wherein the cancer cell comprises a first antigen on the surface of the cancer cell, under conditions whereby the first antigen binding portion of the first antibody or fragment thereof binds the first antigen on the surface of the cancer cell, wherein the first antigen is CD20, the first antigen binding portion is a CD20 binding portion, and the targeting ligand is tetrazine; and (b) contacting the cancer cell of step (a) with a natural killer (NK) cell comprising a targeting agent specific for the targeting ligand of the first antibody or fragment thereof, wherein the targeting agent is trans-cyclooctene (TCO) and binds in vivo to the targeting ligand of the first antibody or fragment thereof, thereby inducing cytotoxicity in the cancer cell.

2. A method of delivering a natural killer (NK) cell to a cancer cell in a subject having, suspected of having, or at risk of having cancer, the method comprising:

(a) contacting the cancer cell with a first antibody or fragment thereof, wherein the first antibody or fragment thereof comprises a first antigen binding portion and a targeting ligand and wherein the cancer cell comprises a first antigen on the surface of the cancer cell, wherein the first antigen is CD20, the first antigen binding portion is a CD20 binding portion, and the targeting ligand is tetrazine and wherein the first antigen binding portion of the first antibody or fragment thereof binds the CD20 on the surface of the cancer cell; and (b) contacting the cancer cell of step (a) with a NK cell comprising a targeting agent specific for the targeting ligand of the first antibody or fragment thereof, wherein the targeting agent is trans-cyclooctene (TCO) and binds in vivo to the targeting ligand of the first antibody or fragment thereof, thereby delivering the NK cell to the cancer cell in the subject having, suspected of having, or at risk of having cancer.

3. A method of treating cancer in a subject in need thereof, comprising:

(a) administering to the subject an effective amount of a first antibody or fragment thereof, wherein the first antibody or fragment thereof comprises a first antigen binding portion specific for a first cancer antigen and a targeting ligand, wherein the first cancer antigen is CD20, the first antigen binding portion is a CD20 binding portion, and the targeting ligand is tetrazine, and wherein the cancer comprises the CD20 specific for the CD20 binding portion, wherein the CD20 binding portion of the first antibody or fragment thereof binds the CD20 of the cancer; and (b) administering to the subject of (a) an effective amount of a natural killer (NK) cell comprising a targeting agent specific for the targeting ligand of the first antibody or fragment thereof, wherein the targeting agent is trans-cyclooctene (TCO) and binds in vivo to the targeting ligand of the first antibody or fragment thereof, thereby treating the cancer in the subject.

4. The method of claim 3, further comprising administering a second or more antibody or fragment thereof different from said first antibody or fragment thereof, wherein each of the second or more antibody or fragment thereof comprises the same targeting ligand as said first antibody or fragment thereof and a second or more antigen binding portion that is different from the first antigen binding portion of said first antibody or fragment thereof.

5. The method of any one of claim 4, further comprising administering a third antibody or fragment thereof different from said first antibody or fragment thereof and said second antibody or fragment thereof, wherein the third antibody or fragment thereof comprises the same targeting ligand as the first and the second antibody or fragment thereof and a third antigen binding portion that is different from the first and said second antigen binding portion of said first and said second antibody or fragment thereof.

6. The method of claim 3, wherein the NK cell comprises a NK cell line modified to express the targeting agent.

7. The method of claim 3, wherein the NK cell comprises a NK cell from a donor modified ex vivo to express the targeting agent.

8. The method of claim 3, wherein the antibody or fragment thereof is selected from the group consisting of a monoclonal antibody, a Fab fragment, a Fab'-SH fragment, a FV fragment, a scFV fragment, a (Fab')$_2$ fragment, an Fc-fusion protein, an affibody, and any combination thereof.

9. The method of claim 3, wherein the targeting agent and the targeting ligand comprise a bio-orthogonal ligation pair.

10. The method of claim 3, wherein the cancer is breast cancer, lung cancer, lymphoma, colon cancer, prostate cancer, leukemia, multiple myeloma, or any combination thereof.

11. The method of claim 3, wherein the administering step is via a route selected from the group consisting of intravenous, intramuscular, subcutaneous, topical, oral, transdermal, intraperitoneal, intrathecal, intraventricular, intravitreal, intraocular, intraorbital, intranasal, by implantation, by inhalation, by intratumoral, and any combination thereof.

12. The method of claim 3, wherein the subject is a human.

* * * * *

UNITED STATES PATENT AND TRADEMARK OFFICE
CERTIFICATE OF CORRECTION

PATENT NO. : 11,879,010 B2
APPLICATION NO. : 17/934645
DATED : January 23, 2024
INVENTOR(S) : Steven Park It is certified that error appears in the above-identified patent and that said Letters Patent is hereby corrected as shown below:

In the Specification

Column 8, Line 60: Please correct "$10^{10}$ M" to read --$10^{-10}$ M--

Column 12, Line 19: Please correct "(yδ)" to read --($\gamma\delta$)--

Column 12, Line 58: Please correct "F(ab')$_2$" to read --F(ab')2--

Column 12, Line 67: Please correct "F(ab')$_2$" to read --F(ab')2--

Column 13, Line 3: Please correct "F(ab')$_2$" to read --F(ab')2--

Column 13, Line 6: Please correct "F(ab')$_2$" to read --F(ab')2--

Column 13, Line 57: Please correct "P" to read --β--

Column 19, Line 21: Please correct "Cytoxan©" to read --Cytoxan®--

Column 23, Line 54: Please correct "(yδ)" to read --($\gamma\delta$)--

Signed and Sealed this
Sixteenth Day of April, 2024

Katherine Kelly Vidal
*Director of the United States Patent and Trademark Office*